United States Patent
Maris

[11] Patent Number: 6,008,906
[45] Date of Patent: Dec. 28, 1999

[54] OPTICAL METHOD FOR THE CHARACTERIZATION OF THE ELECTRICAL PROPERTIES OF SEMICONDUCTORS AND INSULATING FILMS

[75] Inventor: Humphrey J. Maris, Barrington, R.I.

[73] Assignee: Brown University Research Foundation, Providence, R.I.

[21] Appl. No.: 08/924,792

[22] Filed: Sep. 5, 1997

Related U.S. Application Data

[63] Continuation-in-part of application No. 08/519,666, Aug. 25, 1995, Pat. No. 5,706,094.

[51] Int. Cl.⁶ .................................................. G01N 21/00
[52] U.S. Cl. ..................... 356/432; 356/417; 356/432 T; 356/319; 356/445; 356/381; 356/345; 73/800; 250/226
[58] Field of Search ..................................... 356/417, 432, 356/432 T, 319, 445, 381, 345; 73/800; 250/226

[56] References Cited

U.S. PATENT DOCUMENTS

| | | |
|---|---|---|
| 4,484,820 | 11/1984 | Rosencwaig . |
| 4,522,510 | 6/1985 | Rosencwaig et al. . |
| 4,579,463 | 4/1986 | Rosencwaig et al. . |
| 4,632,561 | 12/1986 | Rosencwaig et al. . |
| 4,636,088 | 1/1987 | Rosencwaig et al. . |
| 4,679,946 | 7/1987 | Rosencwaig et al. . |
| 4,710,030 | 12/1987 | Tauc et al. . |
| 4,750,822 | 6/1988 | Rosencwaig et al. . |
| 4,795,260 | 1/1989 | Schuur et al. . |
| 4,854,710 | 8/1989 | Opsal et al. . |
| 4,952,063 | 8/1990 | Opsal et al. . |
| 4,999,014 | 3/1991 | Gold et al. . |
| 5,042,951 | 8/1991 | Gold et al. . |
| 5,042,952 | 8/1991 | Opsal et al. . |
| 5,074,669 | 12/1991 | Opsal . |
| 5,255,070 | 10/1993 | Pollak et al. . |
| 5,287,169 | 2/1994 | Pollak et al. . |
| 5,303,032 | 4/1994 | Uesu et al. . |
| 5,379,109 | 1/1995 | Gaskill et al. . |
| 5,546,811 | 8/1996 | Rogers et al. . |
| 5,748,317 | 5/1998 | Maris et al. . |
| 5,748,318 | 5/1998 | Maris et al. . |

OTHER PUBLICATIONS

Sumie et al ; "Analysis . . . Measurements"; J. Appl. Physics 76(10), Nov. 15, 1994 pp. 5681–5689.

W. Lee Smith et al. "Ion implant monitoring with thermal wave technology". Appl. Phys.Lett.. vol. 47, No. 6, Sep. 15, 1985. pp. 584–586.

J. Opsal et al. "Thermal and plasma wave depth profiling in silicon". Appl. Phys. Lett. vol. 47 No. 5, Sep. 1, 1985. pp. 498–500.

A. Rosencwaig et al. "Thin–film thickness measurements with thermal waves". Appl. Phys. Lett., vol. 43 No. 2, Jul. 15, 1983. pp. 166–168.

A. Rosencwaig et al. "Detection of thermal waves through optical reflectance". Appl. Phys. Lett., vol. 46 No. 11, Jun. 1, 1985. pp. 1013–1015.

A. Elci et al. "Physics of Ultrafast Phenomena in Solid State Plasmas". Solid–State Electronics, vol. 21, 1978, pp. 151–158.

(List continued on next page.)

*Primary Examiner*—K. P. Hantis
*Attorney, Agent, or Firm*—Ohlandt, Greeley, Ruggiero & Perle, LLP

[57] ABSTRACT

A method for characterizing a sample includes the steps of (a) providing a semiconductor material; (b) applying at least one of an electric field, a pulsed or cw light source, a change in temperature and/or a change in pump pulse intensity to the semiconductor material; (c) absorbing pump light pulses in a portion of the semiconductor material and measuring changes in optical constants as indicated by probe light pulses applied at some time t following the absorption of the pump light pulses; and (e) associating a measured change in the optical constants with at least one of a surface charge, dopant concentration, trap density, or minority carrier lifetime.

29 Claims, 18 Drawing Sheets

OTHER PUBLICATIONS

D.H. Auston et al. "Picosecond Spectroscopy of Semiconductors". Solid–State Electronics, vol. 21, 1978, pp. 147–150.

D. H. Auston et al. "Picosecond Ellipsometry of Transient Electron–Hole Plasmas in Germanium". Physical Review Letters, vol. 32 No. 20. May 20, 1974 pp. 1120–1123.

R.J. Stoner et al. "Kapitza conductance and heat flow between solids at temperatures from 50 to 300K". Physical Review B, vol. 48, No. 22, Dec. 1, 1993 pp. 16 373–16 387.

R.J. Stoner et al. "Measurements of the Kapitza Conductance between Diamond and Several Metals". Physical Review Letters, vol. 68 No. 10, Mar. 9, 1992 pp. 1563–1566.

S. Sumie et al. "A New Method of Photothermal Displacement Measurement by Laser Interferometric Probe". Jpn. J. Appl. Phys. vol. 31 Pt. 1, No. 11, 1992 pp. 3575–3583.

F.E. Doany et al. "Carrier lifetime versus ion–implantation dose in silicon on sapphire". Appl. Phys. Lett. 50(8), Feb. 23, 1987 pp. 460–462.

D.A. Young et al. "Heat Flow in Glasses on a Picosecond Timescale". Dept. of Engineering, Brown University, Providence, RI. 1986. pp. 49–51.

Donald W. Phillion et al., "Subnanosecond relation time measurements using a transient induced grating method", Applied Physics Letters, vol. 27, No. 2, Jul. 15, 1975, pp. 85–86.

"Noninvasive picosecond ultrasonic detection of ultrathin interfacial layers: CFx at the Al/Si interface" by G. Tas, R. J. Stoner and H.J. Maris, Appl Phys. Lett. 61 (15). Oct. 12, 1992 pp. 1787–1789.

"Detection of Thin Interfacial Layers by Picosecond Ultrasonics" by G. Tas, R.J. Stoner J. Maris, G.W. Rubloff, G.S. Oehrlein and J.M. Halbout, Mat. Res. Soc. Symp. Proc. vol. 259 1992 Materials Research Society, pp. 231–236.

"Surface Generation and Detection of Phonons by Picosecond Light Pulses" C. Thomsen et al. Physical Review B. vol. 34, No. 6, Sep. 15, 1986, The American Physical Society, pp. 4129–4138.

"Sound Velocity and Index of Refraction of AlAs Measured by Pico–second Ultrasonics", H.T. Grahn, et al. Appl. Phys. Lett. 53(21), Nov. 21, 1988 pp. 2023–2024.

"Elastic Properties of Silicon Oxynitride Films Determined by Pico–second Acoustics" by H.T. Grahn et al., Appl. Phys. Lett. 53 (23), Dec. 5, 1988, pp. 2281–2283.

"Picosecond optical studies of amorphous diamond and diamondlike carbon: Thermal conductivity and longitudinal sound velocity", Christopher J. Morath, et al, J. Appl. Phys., vol. 76, No. 5, Sep. 1, 1994, p. 2636.

"Study of vibrational modes of gold nanostructures by picosecond ultrasonics", H.N. Lin, et al., J. Appl. Phys. vol. 73, No. 1, Jan. 1, 1993.

"Nondestructive detection of titanium disilicide phase transofrmation by picosecond ultrasonics", H.N. Lin, et al., Applied Physics Letters, No. 61, p. 2700, 1992.

Attenuation of longitudinal–acoustic phonons in amorphous $SiO_2$ at frequencies up to 440 GHz, T.C. Zhu, et al., The American Physical Society 1991.

"Detection of Titanium Silicide Formation And Phase Transformation by Picosecond Ultrasonics", H.N. Lin, et al., Mat. Res. Soc. Proc. Advanced Metalization and Processing for Semiconductor Devices III, vol. 260, p. 221 (1992).

"Ultrasonic Experiments at Ultra–High Frequency with Picosecond Time–Resolution", H.N. Lin, et al., IEEE Ultrasonics Symp. 90.

"Picosecond Optics Studies of Vibrational and Mechanical Properties of Nanostructures ", H. J. Maris, et al., AMD–vol. 140, Acousto–Optics and Acoustic Microscopy ASME 1992.

"Time–resolved study of vibrations of a–Ge:H/a–Si:H multilayers", T.H. Grahn, et al Physical Review B, vol. 38, No. 9, Sep. 15, 1988.

"Picosecond Ultrasonics", Holger T. Grahn, et al., IEEE Journal of Quantum Electronics, vol. 25, No. 12, Dec. 1989.

Nondestructive Testing of Microstructures by Picosecond Ultrasonics, H.N. Lin, et al., Journal of Nondestructive Evaluation, vol. 9, No. 4, 1990.

"Phonon Attenuation and Velocity Measurements in Transparent Materials by Picosecond Acoustic Interferometry", H.N. Lin, et al. Journal of Applied Physics, vol. 69, p. 3860 (Apr. 1991).

"Studies of High–Frequency Acoustic Phonons Using Picosecond Optical Techniques", H.J. Maris, et al., Phonon Scattering in Condensed Matter 5, Eds. A.C. Anderson, J.C. Wolfe, Springer, Berlin, 1986, p. 374.

"Picosecond Photoinduced Electronic and Acoustic Effects In a–Si:H Based Multilayer Structures", H.T. Grahn, et al., Journal of Non–Crystalline Solids 97&98 (1987) p. 855–858.

"Picosecond Acoustics As A Non–Destructive Tool For The Characterization of Very Thin Films", C. Thomsen, et al., Thin Solid Films, 154 (1987) pp. 217–223.

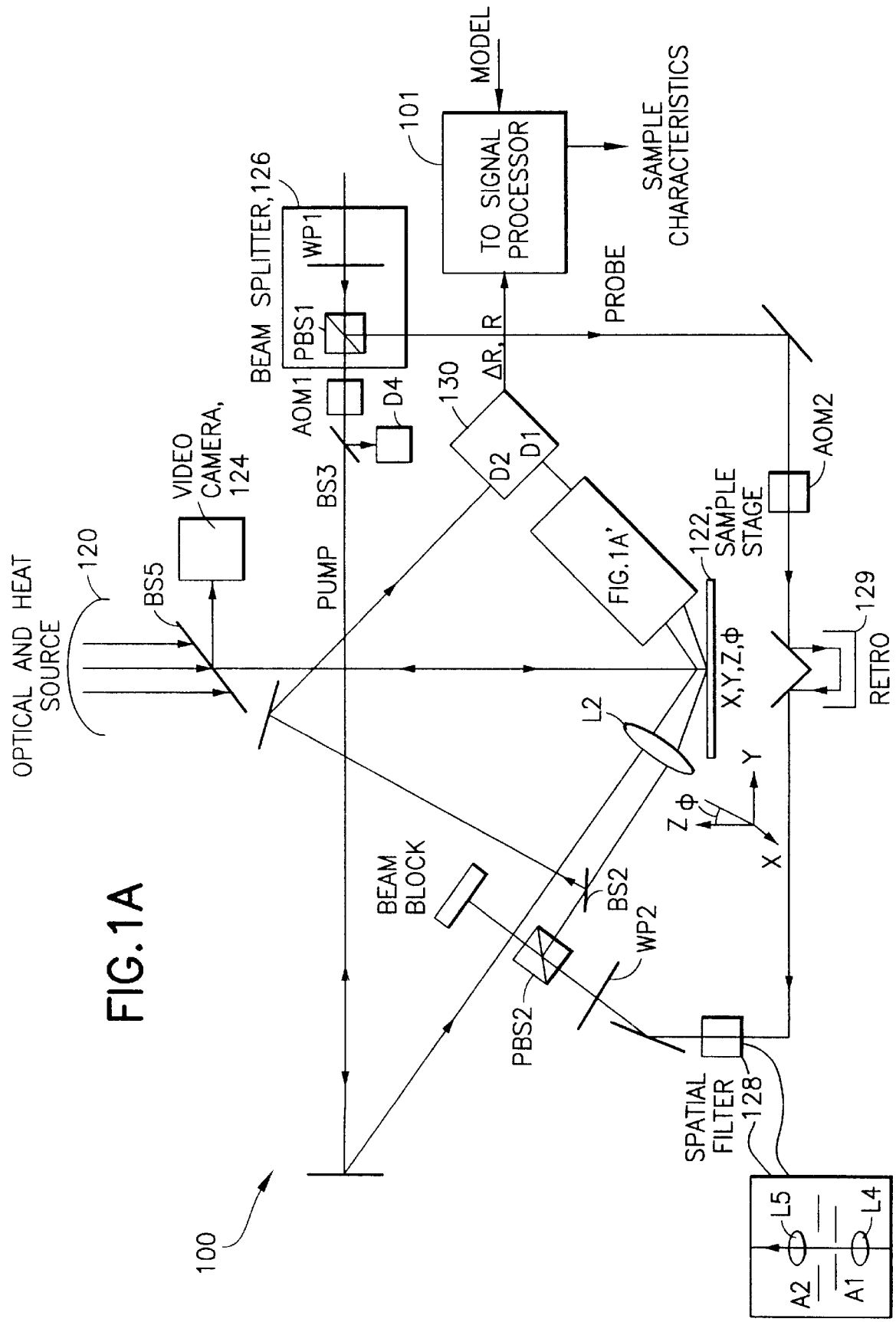

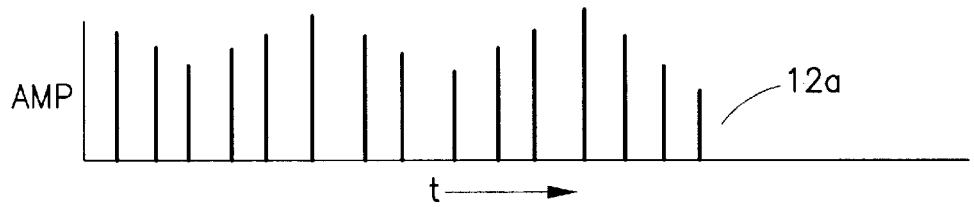
FIG.2
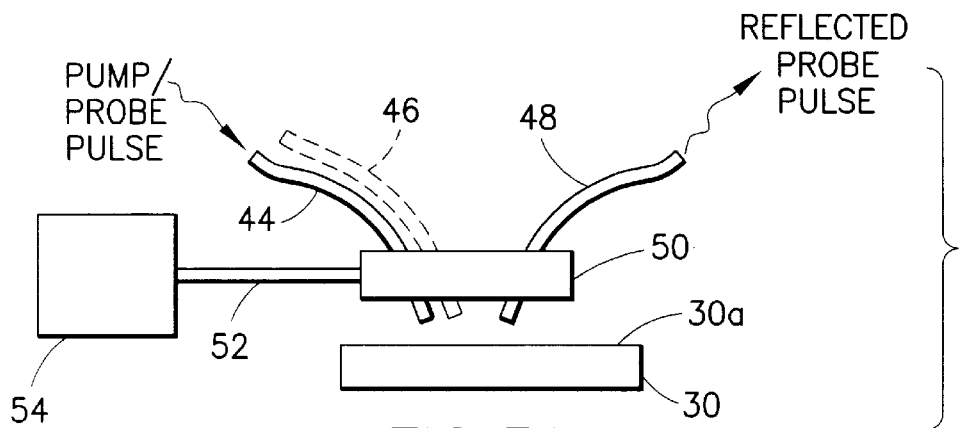
FIG.3A
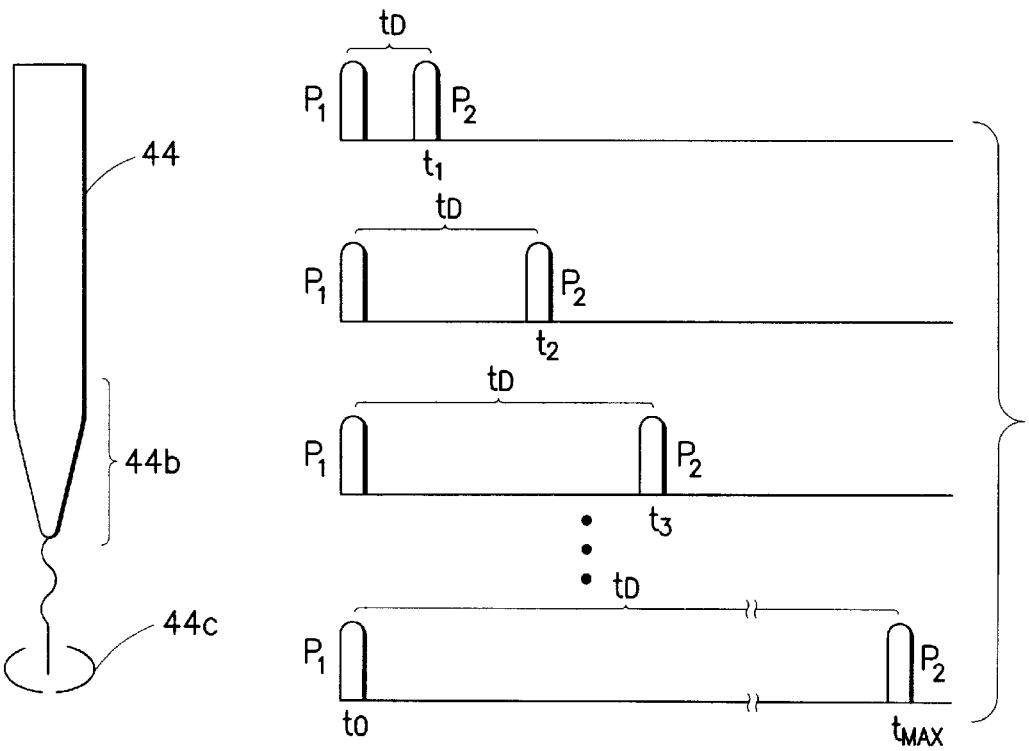
FIG.3B
FIG.9

OPTICAL METHOD FOR THE CHARACTERIZATION OF THE ELECTRICAL PROPERTIES OF SEMICONDUCTORS AND INSULATING FILMS

CROSS-REFERENCE TO A RELATED PATENT APPLICATION

This patent application is a continuation-in-part of U.S. patent application Ser. No. 08/519,666, filed Aug. 25, 1995 now Pat. No. 5,706,094, entitled "Ultrafast Optical Technique for the Characterization of Altered Materials", by Humphrey J. Maris, the disclosure of which is incorporated by reference herein in its entirety.

FIELD OF THE INVENTION

This invention relates generally to a method and apparatus for characterizing a sample using electromagnetic radiation and, in particular, relates to a system for determining at least one electrical property of ion-implanted semiconductors, and semiconductors doped by other methods, and the electrical properties of films deposited onto semiconductor material.

BACKGROUND OF THE INVENTION

Currently in the semiconductor industry there is great interest in monitoring the presence of charge in insulating layers deposited onto semiconductor surfaces. Such charges may be indicative of contamination or defects in these layers which may affect the performance of semiconductor devices.

Current techniques for measuring charge in insulating layers include the following.

A first technique is capacitance-voltage pro filing in which the capacitance of an electrode in intimate contact with a sample is measured as a function of an applied bias voltage and, possibly, frequency. References in this regard are S. M. Sze, "Physics of Semiconductor Devices", New York: John Wiley and Sons, 1969, and also A. S. Grove "Physics and Technology of Semiconductor Devices", New York: John Wiley and Sons, 1967. In a variation of this method a small amount of liquid mercury may be placed in contact with the sample through the use of a small capillary.

A disadvantage of this technique is that it is necessary to have an electrode in contact with the sample.

A second known approach employs a surface photovoltage technique. In this technique a voltage is applied to the surface of the sample by means of an electrode, and the sample is illuminated with a low-intensity light source, such as a light-emitting diode, whose intensity is modulated at a low frequency, for example 10 kHz.

A disadvantage of this technique is that either a contacting electrode is required or, alternatively, an electrode which can deposit charge onto the surface of the sample.

A further approach is known as Deep Level Transient Spectroscopy (DLTS). In this technique the temperature is slowly swept and the charges are progressively released from their trapping sites. The resulting change in capacitance is measured to infer the density of charge trapping centers.

However, this technique also requires that an electrical contact be made to the sample.

Furthermore, none of techniques are well-suited to the study of very small areas of a sample because the sensitivity decreases with decrease in the area that is probed.

In the semiconductor industry certain materials such as silicon, germanium, and gallium arsenide are frequently doped with impurities so as to change their electrical or mechanical properties. These impurities may be introduced by means of ion implantation or by means of in-diffusion from a solid, liquid or gas source. Associated with the introduction of such impurities is an amount of crystalline damage whose characteristics depend on the method by which they are introduced. A variety of ions are commonly used for this purpose including B, P, Ga, Ge, F, Si, B11, BF2, Sb, In, As and hydrogen. In the case of implantation, these ions are accelerated to an energy which may be as low as a few keV or as high as several hundred keV, and are then directed at the surface of the material. After entering the material an ion loses energy by collisions with the atoms of the material. These collisions result in damage to the material, such as displacements of atoms from their normal crystalline positions. For sufficiently high ion doses parts of the material may become amorphous rather than crystalline. The material is thus modified as a result of the damage that occurs (also referred to as the generation of defect sites) and as a result of the introduction of the ions themselves, even if no damage occurs. For in-diffused species, crystal damage in the sample, such as a substrate, may occur as the diffusing atoms displace sample atoms from their lattice sites. The extent of the damage depends on the size of the sample and the diffusing atoms, the nature of the diffusion source (solid, liquid, gas), the concentration of diffusion species in the source, and the details of the thermal process used to drive them into the substrate. It is also possible for there to be no crystal damage (e.g. if the diffusing atoms are small compared to the lattice constant of the sample). In such cases, diffusing atoms may occupy interstitial sites in the sample, and so may alter the local electronic and optical characteristics of the sample.

The material modification generally occurs in a surface layer or region the depth of which can vary from less than 100 Angstroms for low energy ions to several microns (e.g. when high energy ions are used). The dosage, i.e. the number of ions introduced per unit area of the surface of the material, can be varied over a wide range for implanted species by controlling the ion beam current and the time for which the ion beam is directed at the material. For the in-diffusion case the dosage can be controlled varying the thermal cycle or the source concentration. Currently in the semiconductor industry, implant doses as low as $10^{10}$ ions per $cm^2$ and as high as $10^{18}$ ions per $cm^2$ are used for different purposes. Both the material damage and the introduction of the ions results in a change in the electrical properties of the material in the vicinity of the surface where the ions are introduced. Some of the damage to the crystalline structure can be removed by thermally annealing the material.

In the fabrication of semiconductor chips, ion implantation or in-diffusion may be used at a number of stages of the process. Typically, an implant is restricted to predetermined areas, i.e. the implant is patterned. Similarly, in-diffused species may be added in a pattern by masking regions with an impenetrable, heat resistant layer such as $SiO_2$ or nitride. It is important to be able to monitor the dosage and to confirm that the correct regions have been implanted or doped by in-diffusion. Since these regions may be very small, it is important for a measurement technique to have very high spatial resolution. Also, and to avoid unintentionally contaminating the sample during the measurement, it is desirable that a non-contact measurement method be used.

A number of different techniques have been used or proposed for the evaluation of ion-implanted materials, including Rutherford back-scattering, Raman spectroscopy, and sheet resistance measurements. Some of these techniques have also been used to characterize samples to which foreign atoms have been introduced by in-diffusion.

Yet another technique which has been used to characterize ion implants employs a 100% intensity modulated laser beam with modulation frequency ω that is directed at a semiconductor surface, as described by opsal et al., Method and Apparatus For Evaluating Surface and Subsurface Features in a Semiconductor", U.S. Pat. No. 4,854,710. The light that is absorbed in the sample generates an electron-hole plasma, and also a heavily damped thermal wave close to the surface of the sample. Both the plasma and the thermal wave oscillate at frequency ω. These forced plasma and thermal oscillations give rise to small oscillations in the optical reflectivity of the sample which can be measured by means of a probe laser directed onto the same spot as the modulated laser. The amplitude and phase of the small oscillatory component at frequency ω arising in the intensity of the reflected probe beam depend strongly on ω, and also can be affected by the presence of ion implants and related damage in the semiconductor. Thus a measurement of this oscillatory component can be used as a defect or ion implant monitor.

Reference in this regard can also be had to J. Opsal, "Method and Apparatus for Evaluating Ion Implant Levels in Semiconductors", U.S. Pat. No. 5,074,669. In this technique, both the unmodulated component of the reflected probe beam, and the component modulated at frequency ω, are measured and analyzed. In all of the above described techniques the modulation frequency of the pump beam is typically below 10 MHz.

Photo-acoustic displacement measurements (PAD) have also been shown to be sensitive to ion-implant dosage, as described by S. Sumie et al., Jap. J. Appl. Phys. 35, 3575 (1992), and S. Sumie, et al., J. Appl. Phys. 76, 5681 (1994). In these experiments the acoustic displacement is periodic at a frequency of 87 kHz. The measurement is designed so that changes in optical reflectivity due to the electrons and holes excited in the material are not detected.

The optical methods mentioned above generally use periodically-modulated continuous wave pump beams to excite the material. The frequency of the modulation is typically in the range below 10 MHz. However, this range of modulation frequencies can adversely impact the sensitivity of the measurement system and an ability to "profile" the impurities or damage distribution, and may also cause the system to be sensitive to surface effects.

The thermal and electrical properties of materials have also been studied using optical pulse techniques. Short light pulses (duration 100 psec or less) have been used to heat a metal film on a semiconductor dielectric substrate. A time-delayed probe pulse (duration also 100 psec or less) is used to measure the change in the optical reflectivity of the metal film, and from this change the rate at which the film cools by thermal conduction into the substrate can be determined. Reference in this regard can be had to Young et al., Heat Flow in Glasses on a Picosecond Timescale in Phonon Scattering in Condensed Matter V, edited by A. C. Anderson and J. P. Wolfe, (Springer, Berlin, 1986), p. 49; to Stoner et al., Measurements of the Kapitza Conductance between Diamond and Several Metals Phys. Rev. Lett. 68, 1563 (1992); and to Stoner and Maris, Kapitza Conductance and Heat Flow Between Solids at Temperatures from 50 to 300 K, Phys. Rev. B48, 16373 (1993).

Short light pulses have been used to excite electrons and holes in semiconductors, and the change in optical reflectivity that occurs as a result of the excited carriers has been measured with a short probe light pulse. In this regard reference can be made to Auston et al., Picosecond Ellipsometry of Transient Electron-Hole Plasmas in Germanium, Phys. Rev. Lett. 32, 1120 (1974); to Auston et al., Picosecond Spectroscopy of Semiconductors, Solid State Electronics 21, 147 (1978); and to Elci et al., Physics of Ultrafast Phenomena in Solid State Plasmas, Solid State Electronics 21, 151 (978)). This work has generally been directed towards achieving an understanding of how the electrons and holes relax and diffuse, rather than as a means for sample characterization.

In a paper entitled "Carrier Lifetime Versus Ion-Implantation Dose in silicon on Sapphire", F. E. Doany et al., Appl. Phys. Lett. 50(8), Feb. 23, 1987 (pp. 460–462), a report is made of studies conducted on a silicon film of thickness 0.5 micron on a sapphire substrate. The authors employed 70 femtosecond pulses that were generated at a 100 MHz rate, the pump pulses are said to be chopped at a 1 kHz rate, and the probe pulses were obtained from the pump pulses. A change in reflectivity over time was obtained from a photodetector. In this experiment the excited carriers could not enter the substrate because of the large band gap of the sapphire, and hence were confined to the silicon film. Consequently, the electrons and holes were distributed approximately uniformly throughout the thickness of the silicon film, and this assumption was made in the analysis of the data by these authors. It was demonstrated that the lifetime of the excited free carriers was influenced by the implantation dose of $O^+$ ions, and that there is lack of carrier lifetime dependence above an $O^+$ implant dose of $3\times10^{14}$ $cm^{-2}$. It is important to note that in this approach the generated heat cannot readily dissipate and the temperature of the sample can become high.

In a nondestructive ultrasonic technique described in U.S. Pat. No. 4,710,030 (Tauc et al.), a very high frequency sound pulse is generated and detected by means of an ultrafast laser pulse. The sound pulse is used to probe an interface. The ultrasonic frequencies used in this technique typically are less than 1 THz, and the corresponding sonic wavelengths in typical materials are greater than several hundred Angstroms. It is equivalent to refer to the high frequency ultrasonic pulses generated in this technique as coherent longitudinal acoustic phonons.

In more detail, Tauc et al. teach a system wherein a transient optical response arises from mechanical waves (stress pulses) which are generated by a pump pulse and which propagate in the sample. Tauc et al. describe the use of pump and probe beams having durations of 0.01 to 100 psec. These beams may impinge at the same location on a sample's surface, or the point of impingement of the probe beam may be shifted relative to the point of impingement of the pump beam. In one embodiment the film being measured can be translated in relation to the pump and probe beams. The probe beam may be transmitted or reflected by the sample. In a method taught by Tauc et al. the pump pulse has at least one wavelength for non-destructively generating a stress pulse in the sample. The probe pulse is guided to the sample to intercept the stress pulse, and the method further detects a change in optical constants induced by the stress pulse by measuring an intensity of the probe beam after it intercepts the stress pulse.

In one embodiment a distance between a mirror and a corner cube is varied to vary the delay between the impingement of the pump beam and the probe beam on the sample. In a further embodiment an opto-acoustically inactive film is studied by using an overlying film comprised of an opto-acoustically active medium, such as arsenic telluride. In another embodiment the quality of the bonding between a film and the substrate can be determined from a measurement of the reflection coefficient of the stress pulse at the boundary, and comparing the measured value to a theoretical value.

The methods and apparatus of Tauc et al. are not limited to simple films, but can be extended to obtaining information about layer thicknesses and interfaces in superlattices, multilayer thin-film structures, and other inhomogeneous films. Tauc et al. also provide for scanning the pump and probe beams over an area of the sample, as small as 1 micron by 1 micron, and plotting the change in intensity of the reflected or transmitted probe beam.

OBJECTS OF THE INVENTION

It is a first object of this invention to provide an improved method for the non-destructive evaluation of semiconductors through the use of at least one short light pulse to excite electrons and holes in the semiconductor, and an optical probe to measure the resulting change in the optical constants of the semiconductor as a function of time.

It is a further object of this invention to nondestructively measure charge with micron or submicron spatial resolution in a sample.

It is another object of this invention to provide a non-destructive, non-contact method to determine dopant concentration, trap density, and minority carrier lifetimes in a small area of a semiconductor material.

SUMMARY OF THE INVENTION

This invention teaches a method and a system for the characterization of ion-implanted and other materials through the use of a short pump light pulse to excite the material to be investigated, and an optical probe to examine the material a short time after the application of the pump pulse. A time-dependent change in the optical constants of the material, which may be manifested by a change in, by example, reflectivity or polarization, is measured and is associated with at least one characteristic of an introduced chemical species. By example, a change in reflectivity can be associated with the density of an implanted chemical species and/or with an energy at which the chemical species was implanted. In one embodiment of this invention a transient grating can be established at the surface of the sample for providing a non-uniform distribution of electrons and holes in the sample.

The method and apparatus in accordance with this invention can be employed in conjunction with a measurement of one or more of the following effects arising from a time-dependent change in the optical constants of the sample due to the application of at least one pump pulse: (a) a change in reflected intensity; (b) a change in transmitted intensity; (c) a change in a polarization state of the reflected and/or transmitted light; (d) a change in the optical phase of the reflected and/or transmitted light; (e) a change in direction of the reflected and/or transmitted light; and (f) a change in optical path length between the sample's surface and a detector.

In accordance with an embodiment of this invention the above-described and other problems are overcome and the objects of the invention are realized by a method and system wherein a pump light pulse is absorbed in an area of a sample to be studied. A probe light pulse is used to measure the change in optical reflectivity $\Delta R(t)$ as a function of the time t after the application of the pump pulse. In variations of the method the response $\Delta R(t)$ is measured as a function of (1) an electric field applied to the surface of the sample, and/or (2) the intensity of the pump light beam, and/or (3) intensity of an additional source of illumination (such as a laser source with a continuous spectrum) which may be continuous or pulsed, and/or (4) temperature.

The number and spatial distribution of the carriers excited by the pump light pulse will change with time as a result of the following processes.

In a first process the number and spatial distribution of the carriers excited by the pump light pulse change with time by diffusion away from or towards the surface of the sample. The rate of this diffusion is strongly influenced by an amount of implantation or other damage, and to a lesser degree by a density of impurities in the sample.

In a second process the number and spatial distribution of the carriers excited by the pump light pulse drift under the influence of the electric fields in the sample. Such fields may arise from, for example, electrically charged defects in the sample, and also from gradients in the concentration of electrically active dopant ions. Electric fields may also arise near the surface of a semiconductor sample due to the presence of electrical charge embedded in the surface, or in a material (such as an oxide) disposed on the surface of the semiconductor. In such a case the magnitude and gradient of the electric field in the semiconductor depends on the doping concentration within the semiconductor as well.

In a third process the number and spatial distribution of the carriers excited by the pump light pulse depend on recombination. The recombination rate of the carriers is governed by the density and distribution of recombination centers in the sample. These centers may have been created during the implantation process, or may be associated with impurities introduced intentionally or unintentionally into the sample material, for example, by doping by some means other than implantation.

A measurement of $\Delta R(t)$, combined with a suitable analysis, is shown to be useful to determine the surface charge, dopant concentration(s), trap density, and minority carrier lifetimes.

An electric field applied externally to the sample leads to a change in the time-dependence of the carrier distribution. An analysis of this change can give further information about the quantities that are to be determined. The electric field may be applied by one or more of the following methods.

In a first method a semi-transparent electrode is deposited on top of the sample, the electrode having an area at least the size of the focused pump and probe beams.

In a second method a semi-transparent electrode is provided in close contact with the surface of the sample.

In a third method an electrode with a tapered tip is held in close proximity with the surface of the sample in order to induce a known amount of charge on the surface of an insulating layer.

A change in the intensity of the pump beam changes the number of carriers excited in the sample. For each intensity of the pump beam the transient change in the optical reflectivity $\Delta R(t)$ has a different functional form. By example, for two different pump intensities $I_1$ and $I_2$ the measured changes in reflectivity are $\Delta R_1(t)$ and $\Delta R_2(t)$, respectively. Then, the ratio of $\Delta R_1(t)$ to $\Delta R_2(t)$ depends on the particular time t that is considered, i.e. $\Delta R_1(t)$ and $\Delta R_2(t)$ do not satisfy the relation $\Delta R_1(t) = c\, \Delta R_2(t)$ with c a constant independent of time. Thus, it can be advantageous to further characterize a sample through measurement of ΔR(t) as a function of the intensity, or wavelength, or wavelength distribution, of such illumination.

A change in temperature of the sample modifies the number of carriers present before the application of the pump pulse, and will also change the rate at which carriers are trapped. Consequently, ΔR(t) is modified by such a change in sample temperature. Thus, it may be advantageous to make measurements as a function of temperature, or to make all measurements at one specified temperature. This technique enables measurements to be made under conditions such that the results are most sensitive to a particular attribute of greatest interest (for example, surface charge, dopant concentration, trap density, or minority carrier lifetime).

The sample parameters are determined by comparison of the measured data with data from reference samples or by comparison with simulations. The simulations are carried out accounting for the change in the optical properties of the sample as a function of time due to the temporal behavior of the electrons and holes injected by the pump pulses.

BRIEF DESCRIPTION OF THE DRAWINGS

The above set forth and other features of the invention are made more apparent in the ensuing Detailed Description of the Invention when read in conjunction with the attached Drawings, wherein:

FIG. 1A' illustrates a portion of FIG. 1A in greater detail;

FIG. 2 illustrates a pulse train of pump beam pulses having an overlying low frequency intensity modulation impressed thereon;

FIG. 3A illustrates a further embodiment wherein one or more optical fibers are positioned for delivering the pump beam and/or probe beam and for conveying away the reflected probe beam;

FIG. 3B illustrates a terminal end of a fiber optic that has been reduced in cross-sectional area for delivering an optical pulse to a small surface area of a sample;

FIG. 9 illustrates a timed sequence of a plurality of consecutive pump pulses and corresponding probe pulses;

DETAILED DESCRIPTION OF THE INVENTION

In accordance with the teaching of this invention, a light pulse is directed onto a sample, and is partially absorbed by electronic carriers in the sample, which subsequently transfer their energy to the materials comprising the sample. Associated with the transfer of energy is a small, localized transient change in the sample's optical response. That is, there is manifested at least one transient and measurable response of the sample to the pump pulse of optical radiation. A measured transient response or responses can include at least one of a measurement of a modulated change ΔR in an intensity of a reflected portion of a probe pulse, a change ΔT in an intensity of a transmitted portion of the probe pulse, a change ΔP in a polarization of the reflected probe pulse, a change Δφ in an optical phase of the reflected probe pulse, and a change in an angle of reflection Δβ of the probe pulse, each of which may be considered as a change in a characteristic of a reflected or transmitted portion of the probe pulse. The transient response of the sample to the pump pulse decays at a rate which depends mainly on the rates at which the excited electronic carriers transfer their energy to the remainder of the sample, on the electric field, and also on the thermal diffusivities and thicknesses of the materials comprising the sample.

In a presently preferred embodiment of the teaching of this invention, the time-dependence of the change in optical reflectivity $\Delta R(t)$ of the reflected probe beam is of most interest. In this embodiment the magnitude and time dependence of change in the optical reflectivity is determined by the distribution of foreign species and the process(es) by which they are introduced into a sample.

That is, from measurements on a series of test samples it has been found by the inventor that the reflectivity change $\Delta R(t)$, for times in the range 0 to 1000 psec, is particularly sensitive to the level of the ion implant dose. It should be noted that the observed change in reflectivity is typically in the range of $10^{-3}$ to $10^{-5}$.

Figure 1A:
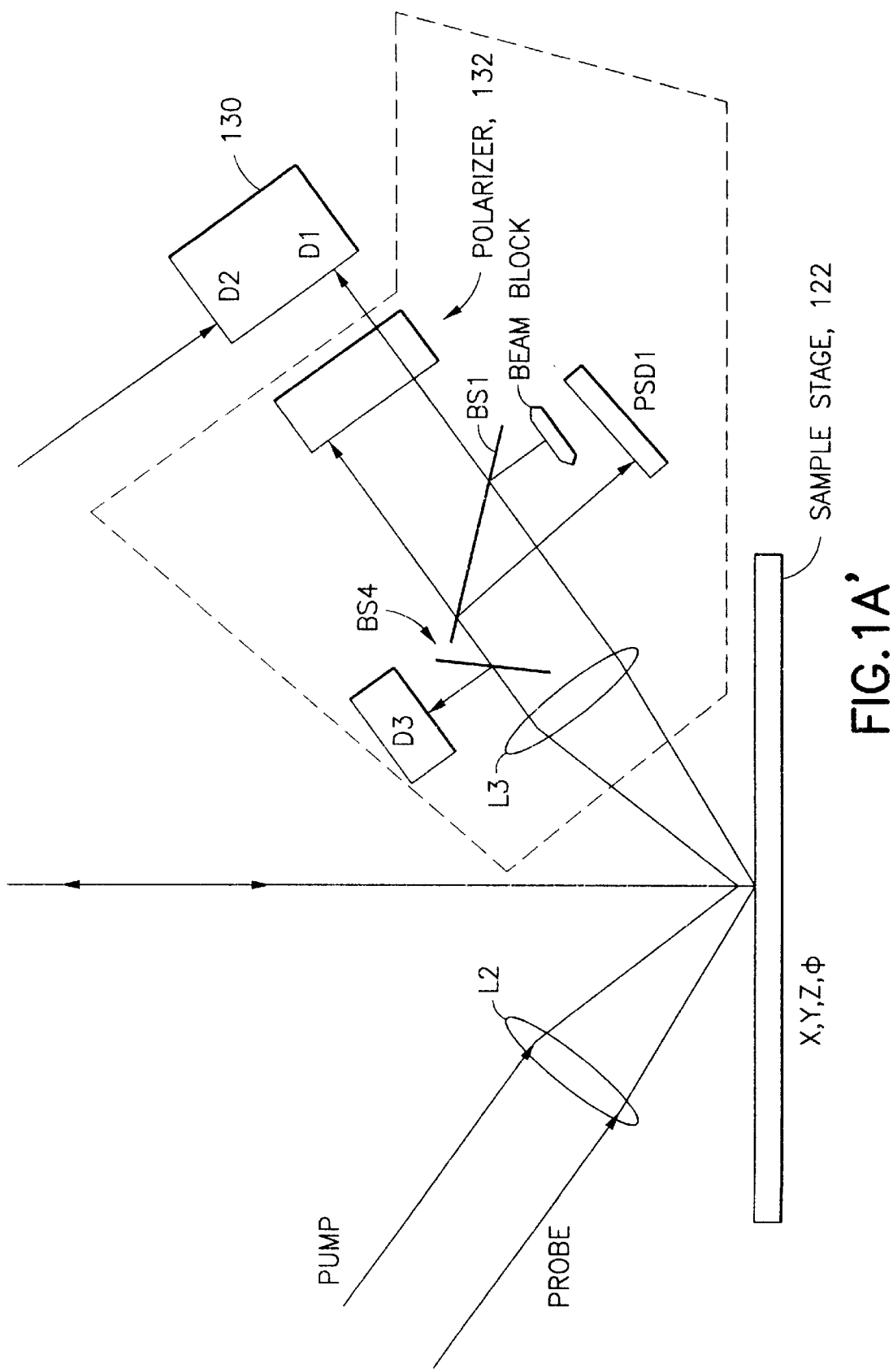
FIG. 1A is a block diagram of a first, presently preferred embodiment of an ultra-fast optical system that is suitable for use in practicing this invention, specifically, a parallel, oblique beam embodiment.

Reference is now made to FIG. 1A and FIG. 1A', collectively referred to below as FIG. 1A, for illustrating a presently preferred embodiment of apparatus 100 suitable for practicing this invention. This embodiment is referred to as a parallel, oblique embodiment.

This embodiment includes an optical/heat source 120, which functions as a variable high density illuminator, and which provides illumination for a video camera 124 and a sample heat source for temperature-dependent measurements under computer control. An alternative heating method employs a resistive heater embedded in a sample stage 122. One advantage of the optical heater is that it makes possible rapid sequential measurements at different temperatures, or at one stabilized temperature.

The video camera 124 provides a displayed image for an operator, and facilitates the set-up of the measurement system. Appropriate pattern recognition software can also be used for this purpose, thereby minimizing or eliminating operator involvement. BS5 is a broad band beam splitter that directs video and a small amount of laser light to the video camera 124. The camera 124 and processor 101 can be used to automatically position the pump and probe beams on a measurement site.

Figure 5:
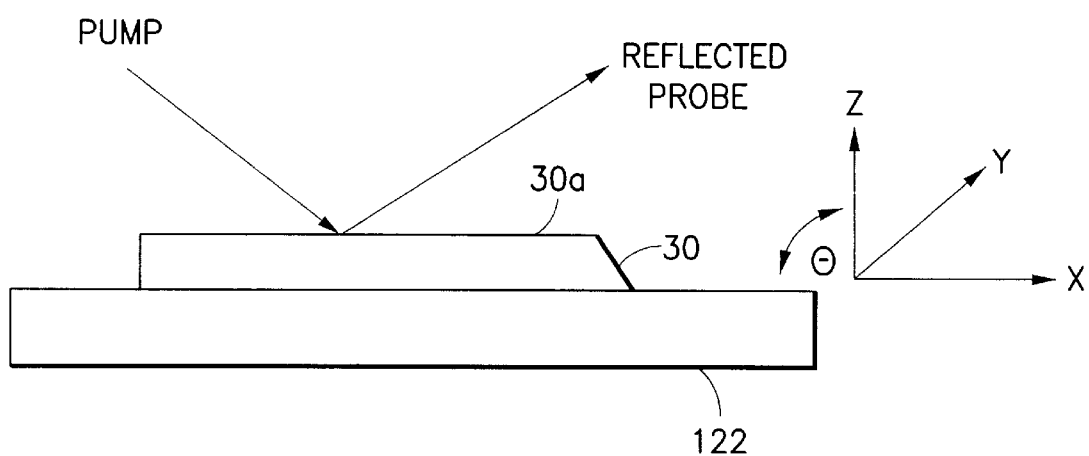
FIG. 5 illustrates the x-y stage positioning mechanism for changing a location where the pump/probe beams intersect the surface of the sample under test.

The sample stage 122 (see also FIG. 5) is preferably a multiple-degree of freedom stage that is adjustable in height (z-axis), position (x and y-axes), and optionally tilt ($\phi$), and allows motor controlled positioning of a portion of the sample relative to the pump and probe beams. The z-axis is used to translate the sample vertically into the focus region of the pump and probe, the x and y-axes translate the sample parallel to the focal plane, and the tilt axes adjust the orientation of the stage 122 to establish a desired angle of incidence for the probe beam. This is achieved via position sensitive detector PSD1 and a signal processor 101, as described below.

In an alternative embodiment, the optical head may be moved relative to a stationary, tiltable stage 122' (not shown). This is particularly important for scanning large objects (such as 300 mm diameter wafers, or mechanical structures, etc.) In this embodiment the pump beam, probe beam, and video signal can be delivered to or from the translatable head via optical fibers or fiber bundles.

The pump-probe beam splitter 126 splits an incident laser beam pulse (preferably of picosecond or shorter duration) into pump and probe beams, and includes a rotatable halfwave plate (WP1) that rotates the polarization of the unsplit beam. WP1 is used in combination with polarizing beam splitter PBS1 to effect a continuously variable split between pump and probe power. This split may be controlled by the computer by means of a motor to achieve an optimal signal to noise ratio for a particular sample. The appropriate split depends on factors such as the reflectivity and roughness of the sample. Adjustment is effected by having a motorized mount rotate WP1 under computer control.

A first acousto-optic modulator (AOM1) chops the pump beam at a frequency of about 1 MHz. A second acousto-optic modulator (AOM2) chops the probe beam at a frequency that differs by a small amount from that of the pump modulator AOM1. The use of AOM2 is optional in the system illustrated in FIG. 1A. Optionally, the AOMs may be synchronized to a common clock source, and may further be synchronized to the pulse repetition rate (PRR) of the laser that generates the pump and probe beams. Optionally an electro-optic modulator can be used in place of acousto-optic modulators AOM1 or AOM2.

A spatial filter 128 is used to preserve at its output a substantially invariant probe beam profile, diameter, and propagation direction for an input probe beam which may vary due to the action of the mechanical delay line shown as a retroreflector 129. The spatial filter 128 includes a pair of apertures A1 and A2, and a pair of lenses L4 and L5. An alternative embodiment of the spatial filter incorporates an optical fiber, as described above. If the profile of the probe beam coming from the mechanical delay line does not vary appreciably as the retroreflector 129 is moved, the spatial filter 128 can be omitted.

WP2 is a second adjustable halfwave plate which functions in a similar manner with PBS2 to the WP1/PBS1 combination of the beam splitter 126. The part of the beam passing through the beam splitter PBS1 impinges on a beam block. Beam splitter BS2 is used to direct a small fraction of the probe beam onto reference detector D2. The output of D2 is amplified and sent through a low pass filter to give an electrical signal LF2 which is proportional to the average intensity of the incident probe beam.

The probe beam after passing through BS2 is focused onto the sample by lens L2. After reflection from the sample the beam is collimated and after passing polarizer 132 is incident on photodetector D1. From the output of D1 two electrical signals are derived. The first signal LF1 is obtained by passing the amplified output of D1 through a low pass filter to give an electrical signal proportional to the average intensity of the incident probe beam. The second signal HF1 is obtained by passing the amplified output of D1 through a high pass filter which passes the frequency of modulation used for AOM1.

The low frequency signals LF1 and LF2 can be used to determine the reflectivity of the sample, after allowance is made for fixed losses in both optical paths. The signal LF2 and the average (dc) output of detector D4 give a measure of the intensity of the pump and probe beams. These signals are fed to a computer, for example the signal processor 101, which in turn controls motorized waveplates WP1 and WP2. The computer is programmed to adjust these waveplates so as to give the desired total optical power and pump/probe ratio for a sample exhibiting a particular reflectivity.

The linear polarizer 132 is employed to block scattered pump light polarization, and to pass the probe beam. The beamsplitter BS1 is used to direct a small part of the pump beam, and optionally a small part of the probe beam, onto a first Position Sensitive Detector (PSD1) that is used for autofocusing, in conjunction with the processor 101 and movements of the sample stage 122. The PSD1 is employed in combination with the processor 101 and the computer-controlled stage 122 (tilt and z-axis) to automatically focus the pump and probe beams onto the sample to achieve a desired focusing condition.

The detector D1 may be used in common for reflectometry, ellipsometry, and transient optical embodiments of this invention. However, the resultant signal processing is different for each application. For transient optical measurements, the DC component of the signal is suppressed, such as by subtracting reference beam input D2, or part of it as needed, to cancel the unmodulated part of D1, or by electrically filtering the output of D1 so as to suppress frequencies other than that of the modulation. The small modulated part of the signal is then amplified and stored. For ellipsometry, there is no small modulated part, rather the entire signal is sampled many times during each rotation of the rotating compensator (see discussion of FIG. 1B below), and the resulting waveform is analyzed to yield the ellipsometric parameters. For reflectometry, the change in the intensity of the entire unmodulated probe beam due to the sample is determined by using the D1 and D2 output signals (D2 measures a signal proportional to the intensity of the incident probe). Similarly, additional reflectometry data can be obtained from the pump beam using detectors D3 and D4. The analysis of the reflectometry data from either or both beams may be used to characterize the sample. The use of two beams is useful for improving resolution, and for resolving any ambiguities in the solution of the relevant equations.

A third beamsplitter BS3 is used to direct a small fraction of the pump beam onto detector D4, which measures a signal proportional to the incident pump intensity. A fourth beamsplitter BS4 is positioned so as to direct a small fraction of the pump beam onto detector D3, which measures a signal proportional to the reflected pump intensity.

Figure 1B:
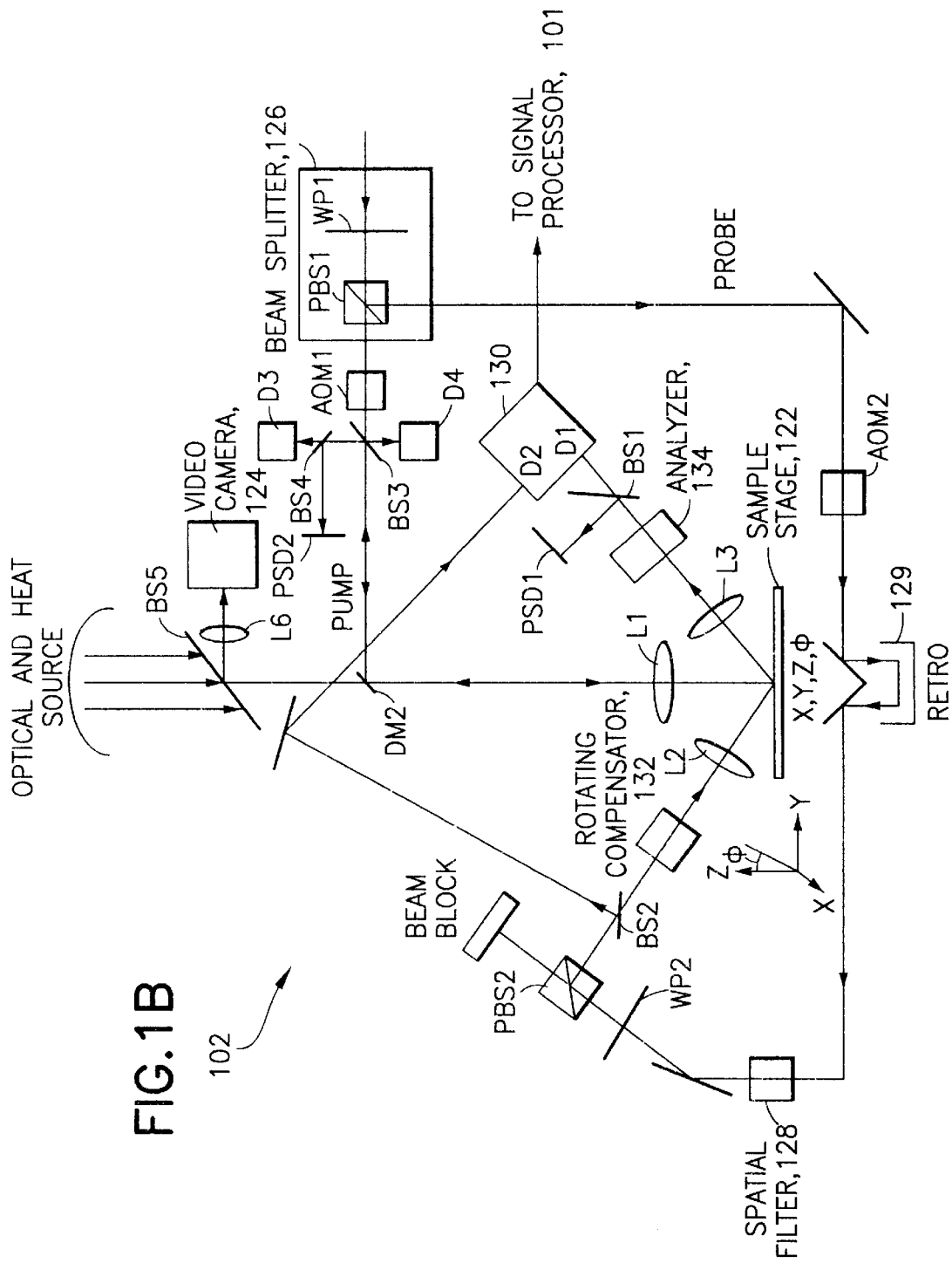
FIG. 1B is a block diagram of a second embodiment of an ultra-fast optical system that is suitable for use in practicing this invention, specifically, a normal pump, oblique probe embodiment.

FIG. 1B illustrates a normal pump beam, oblique probe beam embodiment of apparatus 102. Components labelled as in FIG. 1A function in a similar manner, unless indicated differently below. In FIG. 1B there is provided the above-mentioned rotating compensator 132, embodied as a linear quarter wave plate on a motorized rotational mount, and which forms a portion of an ellipsometer mode of the system. The plate is rotated in the probe beam at a rate of, by example, a few tens of Hz to continuously vary the optical phase of the probe beam incident on the sample. The reflected light passes through an analyzer 134 and the intensity is measured and transferred to the processor 101 many times during each rotation. The signals are analyzed according to known types of ellipsometry methods to determine the characteristics of the sample (transparent or semi-transparent films). This allows the (pulsed) probe beam to be used to carry out ellipsometry measurements.

The ellipsometry measurements are carried out using a pulsed laser, which is disadvantageous under normal conditions, since the bandwidth of the pulsed laser is much greater than that of a CW laser of a type normally employed for ellipsometry measurements.

The ellipsometry measurement capability is useful in performing certain of the embodiments of the method described below, wherein it is required to determine the index of refraction of a film layer disposed over a substrate.

If transient optical measurements are being made, the rotating compensator 132 is oriented such that the probe beam is linearly polarized orthogonal to the pump beam. The analyzer 134 may be embodied as a fixed polarizer, and also forms a portion of the ellipsometer mode of the system. When the system is used for transient optical measurements the polarizer 134 is oriented to block the pump.

The analyzer 134 may be embodied as a fixed polarizer, and also forms a portion of the ellipsometer mode of the system. When used in the ellipsometer mode, the polarizer 134 is oriented so as to block light polarized at 45 degrees relative to the plane of the incident and reflected probe beam.

The embodiment of FIG. 1B further includes a dichroic mirror (DM2), which is highly reflective for light in a narrow band near the pump wavelength, and is substantially transparent for other wavelengths.

It should be noted in FIG. 1B that BS4 is moved to sample the pump beam in conjunction with BS3, and to direct a portion of the pump to D3 and to a second PSD (PSD2). PSD2 (pump PSD) is employed in combination with the processor 101, computer controlled stage 122 (tilt and z-axis), and PSD1 (Probe PSD) to automatically focus the pump and probe beams onto the sample to achieve a desired focusing condition. Also, a lens L1 is employed as a pump, video, and optical heating focussing objective, while an optional lens L6 is used to focus the sampled light from BS5 onto the video camera 124.

Figure 1C:
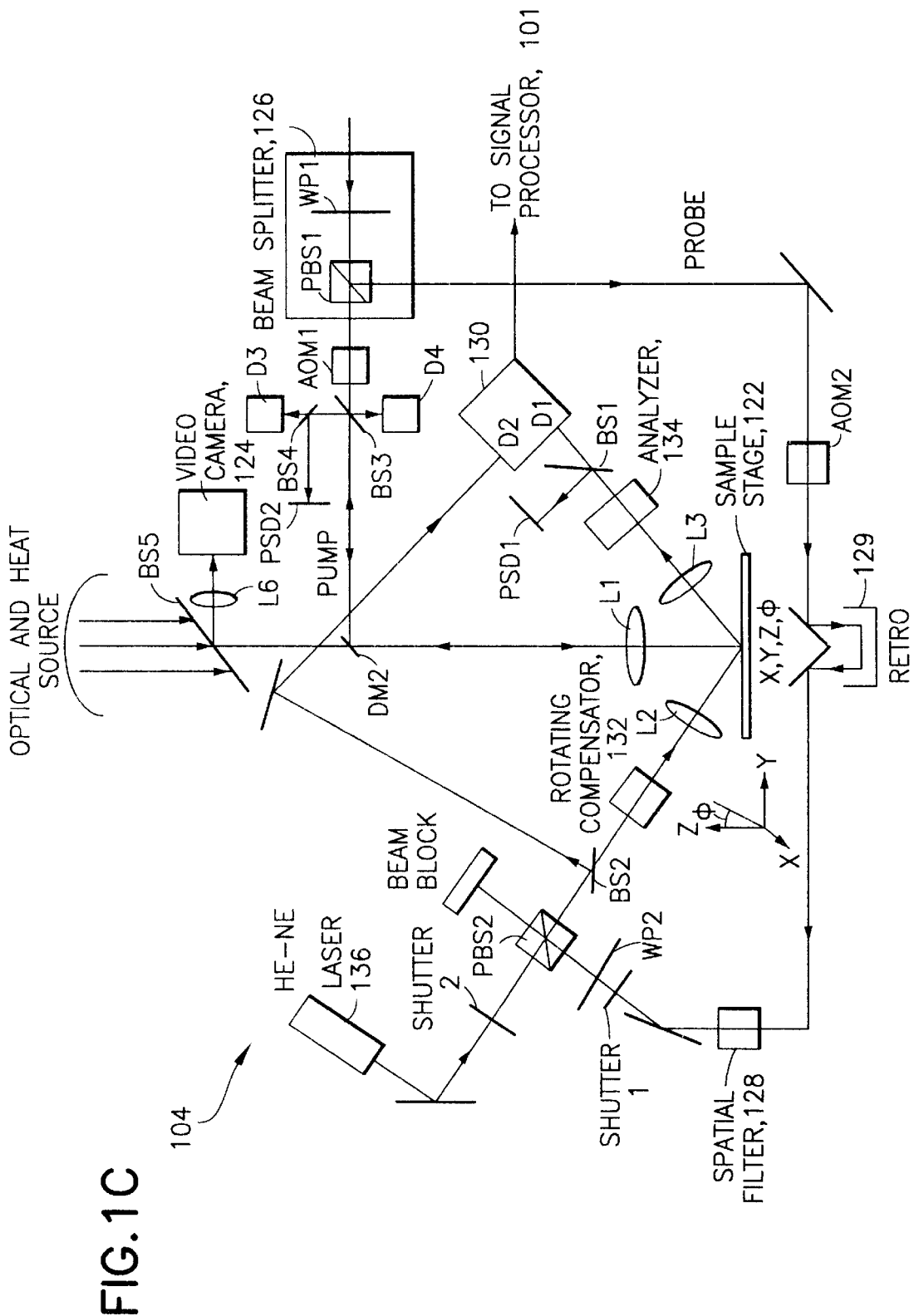
FIG. 1C is a block diagram of a third embodiment of an ultra-fast optical system that is suitable for use in practicing this invention, specifically, a single wavelength, normal pump, oblique probe, combined ellipsometer embodiment.

Reference is now made to FIG. 1C for illustrating an embodiment of apparatus 104, specifically a single wavelength, normal pump, oblique probe, combined ellipsometer embodiment. As before, only those elements not described previously will be described below.

Shutter 1 and shutter 2 are computer controlled shutters, and allow the system to use a He-Ne laser 136 in the ellipsometer mode, instead of the pulsed probe beam. For transient optical measurements shutter 1 is open and shutter 2 is closed. For ellipsometer measurements shutter 1 is closed and shutter 2 is opened. The HeNe laser 136 is a low power CW laser, and has been found to yield superior ellipsometer performance for some films.

Figure 1D:
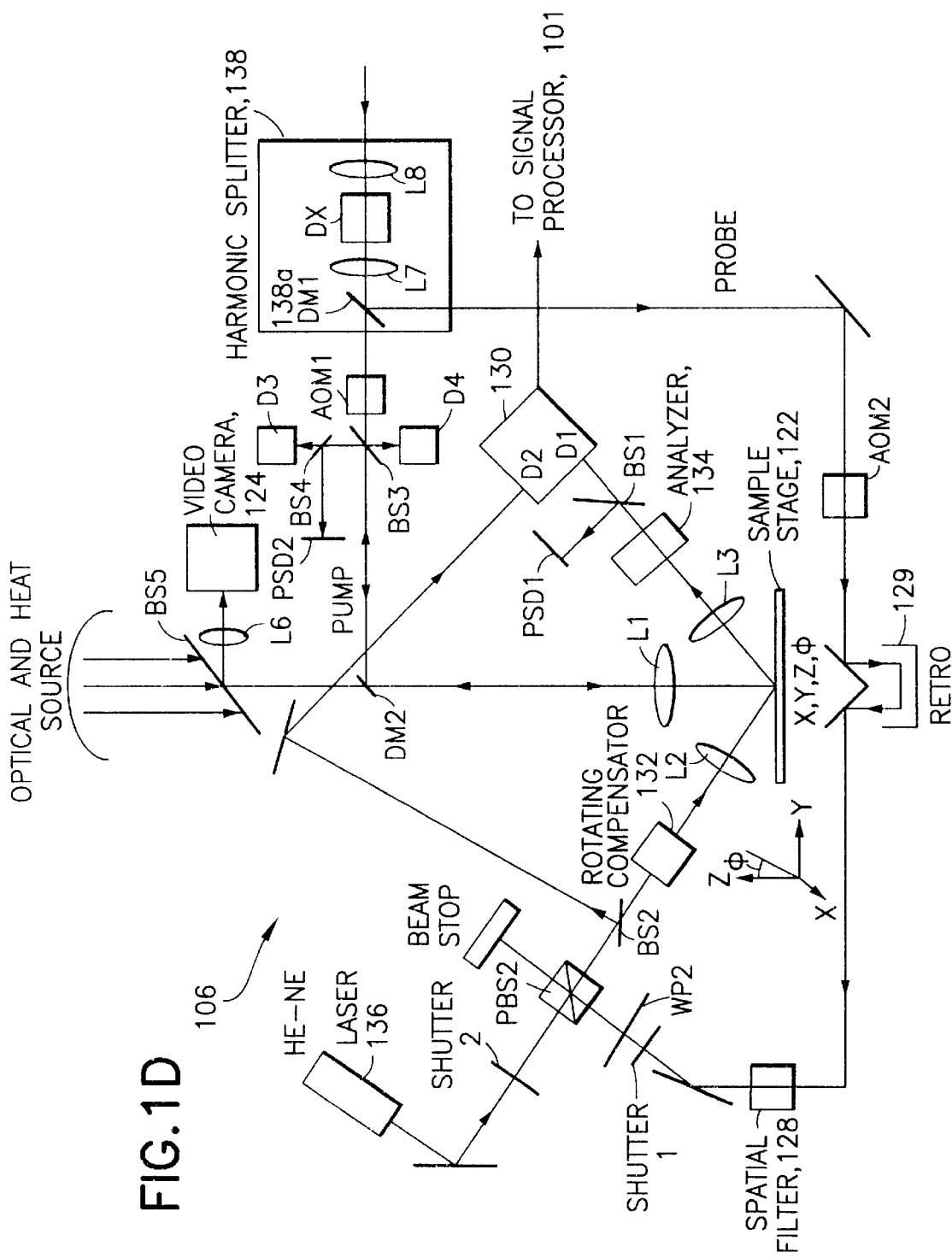
FIG. 1D is a block diagram of a fourth embodiment of an ultra-fast optical system that is suitable for use in practicing this invention, specifically, a dual wavelength, normal pump, oblique probe, combined ellipsometer embodiment.

FIG. 1D is a dual wavelength embodiment 1D of the system illustrated in FIG. 1C. In this embodiment the beamsplitter 126 is replaced by a harmonic splitter, an optical harmonic generator that generates one or more optical harmonics of the incident unsplit incident laser beam. This is accomplished by means of lenses L7, L8 and a nonlinear optical material (DX) that is suitable for generating the second harmonic from the incident laser beam. The pump beam is shown transmitted by the dichroic mirror (DM1 138a) to the AOM1, while the probe beam is reflected to the retroreflector. The reverse situation is also possible. The shorter wavelength may be transmitted, and the longer wavelength may be reflected, or vice versa. In the simplest case the pump beam is the second harmonic of the probe beam (i.e., the pump beam has one half the wavelength of the probe beam).

It should be noted that in this embodiment the AOM2 can be eliminated and instead a color filter F1 can be used in front of the detector D1 in order to reduce the amount of light reaching the detector D1. F1 is a filter having high transmission for the probe beam and the He-Ne wavelengths, but very low transmission for the pump wavelength.

Figure 1E:
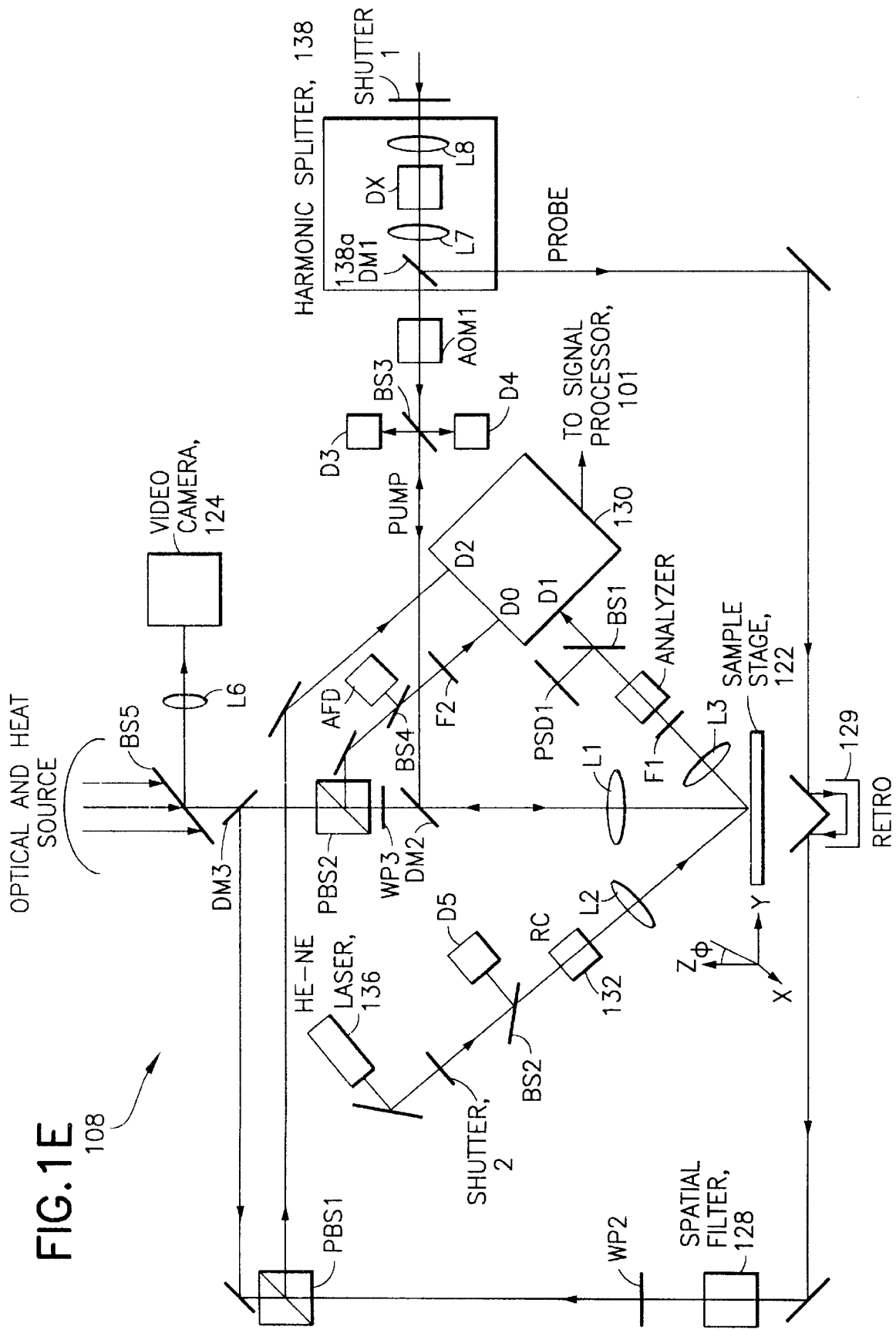
FIG. 1E is a block diagram of a fifth embodiment of an ultra-fast optical system that is suitable for use in practicing this invention, specifically, a dual wavelength, normal incidence pump and probe, combined ellipsometer embodiment.

Finally, FIG. 1E illustrates a normal incidence, dual wavelength, combined ellipsometer embodiment 108. In FIG. 1E the probe beam impinges on PBS2 and is polarized along the direction which is passed by the PBS2. After the probe beam passes through WP3, a quarter wave plate, and reflects from the sample, it returns to PBS2 polarized along the direction which is highly reflected, and is then directed to a detector D0 in detector block 130. D0 measures the reflected probe beam intensity.

In greater detail, WP3 causes the incoming plane polarized probe beam to become circularly polarized. The handedness of the polarization is reversed on reflection from the sample, and on emerging from WP3 after reflection, the probe beam is linearly polarized orthogonal to its original polarization. BS4 reflects a small fraction of the reflected probe onto an Autofocus Detector AFD.

DM3, a dichroic mirror, combines the probe beam onto a common axis with the illuminator and the pump beam. DM3 is highly reflective for the probe wavelength, and is substantially transparent at most other wavelengths.

D1, a reflected He-Ne laser 136 detector, is used only for ellipsometric measurements.

It should be noted that, when contrasting FIG. 1E to FIGS. 1C and 1D, that the shutter 1 is relocated so as to intercept the incident laser beam prior to the harmonic splitter 138.

Based on the foregoing descriptions, a selected one of these presently preferred embodiments of measurement apparatus provide for the characterization of samples in which a short optical pulse (the pump beam) is directed to an area of the surface of the sample, and then a second light pulse (the probe beam) is directed to the same or an adjacent area at a later time. The retroreflector 129 shown in all of the illustrated embodiments of FIGS. 1A–1E can be employed to provide a desired temporal separation of the pump and probe beams.

The apparatus 100, 102, 104, 106 and 108, as described above, are capable of measuring the (1) transient change in the reflectivity of the probe beam. With suitable modifications the apparatus can be used to measure (2) the change $\Delta T$ in the intensity of the transmitted probe beam, (3) the change $\Delta P$ in the polarization of the reflected probe beam, (4) the change $\Delta \phi$ in the optical phase of the reflected probe beam, and/or (5) the change in the angle of reflection $\Delta \beta$ of the probe beam. These quantities may all be considered as transient responses of the sample which are induced by the pump pulse. These measurements can be made together with one or several of the following: (a) measurements of any or all of the quantities (1)–(5) just listed as a function of the incident angle of the pump or probe light, (b) measurements of any of the quantities (1)–(5) as a function of more than one wavelength for the pump and/or probe light, (c) measurements of the optical reflectivity through measurements of the incident and reflected average intensity of the pump and/or probe beams; (d) measurements of the average phase change of the pump and/or probe beams upon reflection; and/or (e) measurements of the average polarization and optical phase of the incident and reflected pump and/or probe beams. The quantities (c), (d) and (e) may be considered to be average or static responses of the sample to the pump beam.

Figure 1F:
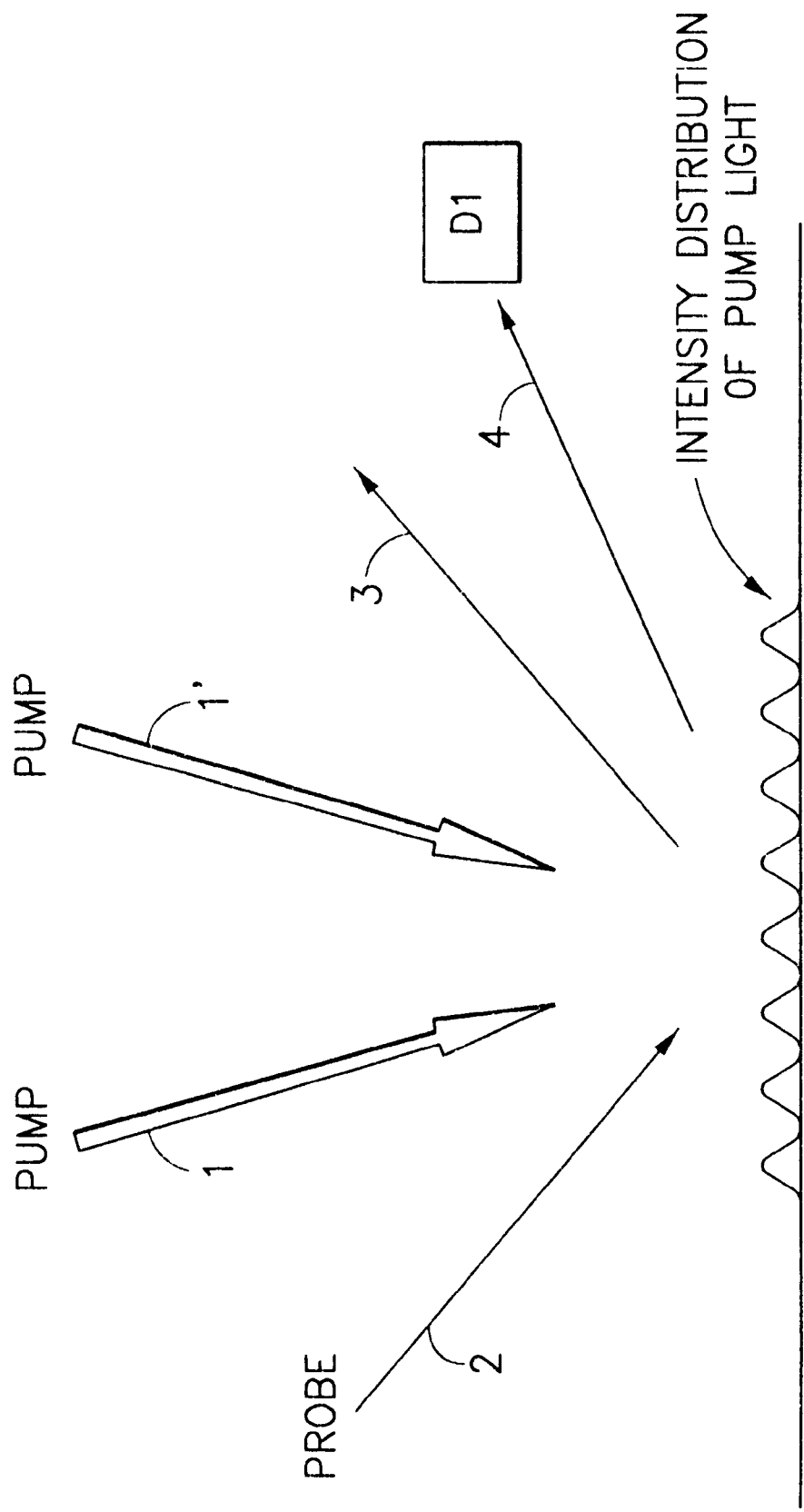
FIG. 1F illustrates the operation of a transient grating embodiment of this invention, wherein the pump pulse is divided and made to interfere constructively and destructively at the surface of the sample.

The five embodiments 100, 102, 104, 106 and 108, as described above, have in common the feature that a sequence of pump pulses are generated and directed at the surface of the sample. Each pump pulse illuminates the same area of the sample with an intensity that varies smoothly across the area. It is also within the scope of this invention to make measurements of the transient optical response by means of the induced transient grating method described by Phillion et al. (D. W. Phillion, D. J. Kuizenga, and A. E. Siegman, Appl. Phys. Lett. 27, 85 (1975)). To induce a transient grating each pump pulse is divided into two or more components by means of a beam splitter or beam splitters, these components then pass through separate optical paths, and are then all directed onto the same area of the surface of the sample. If the different components are directed onto the surface with different angles there will be places within the area where the different components interfere constructively and places where the interference is destructive. Thus the total intensity of the pump light will vary across the sample surface. In the case that only two components 1 and 1' are present, as shown in FIG. 1F, the intensity will vary periodically across the sample surface. The periodicity of the intensity, i.e. the spacing between successive points of maximum intensity, is determined by the wavelength of the pump light and the angles at which the different components of the pump light are incident onto the surface. Then the amount of light absorbed in the structure will vary periodically across the surface, and the number of electrons and holes which are generated by the pump light will vary periodically across the surface. Consequently, the transient changes in the optical properties of the sample which result from the introduction of the electrons and holes will also vary periodically across the surface of the sample. This variation of the transient changes in the optical properties of the sample is equivalent to the production of a transient diffraction grating coinciding with the sample surface. When probe light 2 is incident on the area excited by the pump, a part 4 of the probe light will be diffracted, i.e. a part of the probe light will be reflected in a direction, or directions, away from the direction 3 of specular reflection. Measurement of the intensity of this diffracted probe light by means of the detector D1 as a function of the time delay t between the application of the pump and probe beams provides an alternate method for the characterization of the transient optical response produced by the carriers excited in the sample.

Typical characteristics of the light pulses employed in the systems 100–108 of FIGS. 1A–1E are as follows. The pump pulse has an energy of approximately 0.001 to 100 nJ per pulse, a duration of approximately 0.01 psecs to 100 psec per pulse, and a wavelength in the range 200 nm to 4000 nm. The pulse repetition rate (PRR) is in the range of 100 Hz to 5 GHz and, as is shown in FIG. 2, the pump pulse train may be intensity modulated at a rate of 1 Hz to 100 MHz, depending on the PRR. The pump pulse is focussed to form a spot on the sample surface of diameter in the range of approximately 10 micrometers to 20 micrometers, although smaller spot sizes, and hence smaller lateral resolutions, can also be employed.

Referring to FIG. 3A, it is also within the scope of the teaching of this invention to deliver the pump pulse, or the probe pulse, or both the pump and probe pulses, through an optical fiber 44. Alternatively, a second input fiber 46 can be provided, whereby the pump pulse is delivered through the fiber 44 and the probe pulse is delivered through the fiber 46. Another fiber 48 can also be employed for receiving the reflected probe pulse and delivering same to the photodetector 34. For this embodiment the end of the optical fiber(s) are affixed to and supported by a holding stage 50. The holding stage 50 is preferably coupled through a member 52 to an actuator 54, such as a linear actuator or a two degree of freedom positioning mechanism.

In this manner the reliability and repeatability of the measurement cycle is improved, in that the size and position of the focussed pump, probe, or pump and probe beams on the sample surface are independent of minor changes in the direction or profile of the laser output beams, or changes in the profile of the probe beam associated with the motion of any mechanical stage that may be used to effect the delay $t_D$.

Preferably, the angular orientation between the end of the probe beam delivery fiber and the end of the reflected probe beam fiber is such as to optimize the gathering of reflected probe beam light from the sample surface. It is also within the scope of this invention to use one or more lenses following the fiber or fibers, in order to focus the output beams from the fibers onto the sample surface, or to collect the reflected probe light and to direct it into the fiber 48 of FIG. 3A.

FIG. 3B shows an embodiment wherein a terminal portion 44b of a pump and/or probe beam delivery fiber 44a is reduced in diameter, such as by stretching the fiber, so as to provide a focussed spot 44c having a diameter that is less than the normal range of optical focussing. When coupled with the embodiment of FIG. 3A this enables the pump and or probe optical pulse to be repeatably delivered to a very small region of the sample surface (e.g., to a spot having a diameter≦one micrometer), regardless of any changes that are occurring in the optical path length of the probe beam.

FIG. 9 illustrates various time delays ($t_D$) between the application of a pump pulse (P1) and a subsequent application of a probe pulse (P2), for times ranging from $t_1$ to $t_{MAX}$.

Having thus described a number of presently preferred embodiments of apparatus for obtaining measurements of a sample, the following description will focus on the use of this apparatus with ion-implanted and other sample types.

It is first noted that it is within the scope of this invention to employ computer simulations to calculate the change in the optical reflectivity $\Delta R_{sim}(t)$ of the sample when it is illuminated with a pump pulse of unit energy per unit area of the sample. The simulation may also give a value for the static reflection coefficient of the pump and probe beams. The system measures the transient change $\Delta P_{probe-refl}$ in the power of the reflected probe pulse as determined, for example, by photodiode D1 in FIG. 1C. It also measures the static reflection coefficients of the pump and probe beams from a ratio of the power in the incident and reflected beams. The incident probe power is measured by photodiode D2 in FIG. 1C, the reflected probe power is measured by D1, the incident pump power is measured by D4, and the reflected pump power is measured by D3.

To relate such simulation results for the transient change in the optical reflectivity to the actual system measurement it is advantageous to know: (a) the power of the pump and probe beams; (b) the intensity profiles of these beams; and (c) their overlap on the sample surface.

Suppose first that the pump beam is incident over an area $A_{pump}$ and that within this area the pump intensity is uniform. Then for each applied pump pulse the pump energy absorbed per unit area is $$\frac{P_{pump-inc}}{A_{pump}} \frac{(1 - R_{pump})}{f} \quad (1)$$

where f is the repetition rate of the pump pulse train, and $R_{pump}$ is the reflection coefficient for the pump beam.

Thus, the change in optical reflectivity of the each probe light pulse will be:

$$\Delta R_{sim}(t) \frac{P_{pump-inc}}{A_{pump}} \frac{(1 - R_{pump})}{f} \quad (2)$$

and the change in power of the reflected probe beam will be $$\Delta P_{probe-refl} = P_{probe-inc} \Delta R_{sim}(t) \frac{P_{pump-inc}}{A_{pump}} \frac{(1 - R_{pump})}{f} \quad (3)$$

In a practical system the illumination of the sample does not, in fact, produce a uniform intensity of the incident pump beam. Moreover, the intensity of the probe light will also vary with position on the sample surface. To account for these variations the equation for $\Delta P_{probe-refl}$ is modified to read:

$$\Delta P_{probe-refl} = P_{probe-inc} \Delta R_{sim}(t) \frac{P_{pump-inc}}{A_{effective}} \frac{(1 - R_{pump})}{f} \quad (4)$$

where the effective area $A_{effective}$ is defined by the relation $$A_{effective} = \frac{\int I_{pump-inc}(\vec{r}) dA \int I_{probe-inc}(\vec{r}) dA}{\int I_{pump-inc}(\vec{r}) I_{probe-inc}(\vec{r}) dA} \quad (5)$$

where $I_{probe-inc}(\vec{r})$ and $I_{pump-inc}(\vec{r})$ are respectively the intensities of the probe and pump beams on the surface of the sample. One may consider $A_{effective}$ to be an to area of overlap of the pump and probe beams.

Analogous expressions can be derived for the change in optical transmission $\Delta T(t)$, the change in optical phase $\Delta \phi(t)$, the change in polarization $\Delta P(t)$, and the change $\Delta \beta(t)$ in the angle of reflection of the probe light.

The following quantities can be measured by the system: $\Delta P_{probe-refl}$, $P_{probe-inc}$, $P_{pump-inc}$, $R_{pump}$, $R_{probe}$. A computer simulation gives predicted values for $\Delta R_{sim}(t)$, $R_{pump}$, and $R_{probe}$. Thus, the following comparisons can be made between the simulation and the system measurements in order to determine the characteristics of the sample.

(1) A comparison of the simulated and measured reflection coefficient $R_{pump}$.

(2) A comparison of the simulated and measured reflection coefficient $R_{probe}$.

(3) A comparison of the simulated and measured transient change $\Delta P_{probe-refl}$ in the power of the reflected probe light.

To make a comparison of the simulated and measured change, it can be seen from the preceding equation (4) that it is necessary to know the value of $A_{effective}$. This can be accomplished by one or more of the following methods.

(a) A first method directly measures the intensity variations of the pump and probe beams over the surface of the sample, i.e, $I_{probe-inc}(\vec{r})$ and $I_{pump-inc}(\vec{r})$ as a function of position, and uses the results of these measurements to calculate $A_{effective}$. This is possible to accomplish but requires very careful measurements which may be difficult to accomplish in an industrial environment.

(b) A second method measures the transient response $\Delta P_{probe-refl}$ for a sample on a system S for which the area $A_{effective}$ is known. This method then measures the response $\Delta P_{probe-refl}$ of the same sample on the system S' for which $A_{effective}$ is to be determined. The ratio of the responses on the two systems gives the inverse of the ratio of the effective areas for the two systems. This can be an effective method because the system S can be chosen to be a specially constructed system in which the areas illuminated by the pump and probe beams are larger than would be desirable for an instrument with rapid measurement capability. Since the areas are large for this system it is simpler to measure the intensity variations of the pump and probe beams over the surface of the sample, i.e, $I_{probe-inc}(\vec{r})$ and $I_{pump-inc}(\vec{r})$ as a function of position. This method is effective even if the quantities which enter into the calculation of the simulated reflectivity change $\Delta R_{sim}(t)$ are not known.

(c) A third method measures the transient response $\Delta P_{probe-refl}$ for a sample in which all of the quantities are known which enter into the calculation of the simulated reflectivity change $\Delta R_{sim}(t)$ of the sample when it is illuminated with a pump pulse of unit energy per unit area of the sample. Then by comparison of the measured transient response $\Delta P_{probe-refl}$ with the response predicted from Eq. 4, the effective area $A_{effective}$ is determined.

The above detailed description of methods for relating the simulation results for the transient change in the optical reflectivity and the other transient optical responses is applicable only if the changes in the optical properties induced by the pump pulse are directly proportional to the intensity of this pulse. If the responses are not proportional to the intensity of the pump pulse, it is necessary to use method (a).

It is important that the effective area $A_{effective}$ be stable throughout the course of a sequence of measurements. To ensure this, the apparatus shown in FIGS. 1A–1E incorporate means for automatically focusing the pump and probe beams onto the surface of the sample so as to achieve a reproducible intensity variation of the two beams during every measurement. The automatic focusing system provides a mechanism for maintaining the system in a previously determined state in which the size and relative positions of the beams on the sample surface are appropriate for effective transient response measurements.

It should be noted that for any application in which the amplitude of an optical transient response is used to draw quantitative conclusions about a sample a calibration scheme such as described above is an important feature of the measurement system.

The preceding description of the method for the comparison of the computer simulation results and the system measurements supposes that the several detectors in the measurement system are calibrated. It is contemplated that such a system will use detectors operating in the linear range so that the output voltage V of each detector is proportional to the incident optical power P. For each detector there is thus a constant G such that V=GP. The preceding description assumes that the constant G is known for each and every detector. In the case that this information is not available, the individual calibration factors associated with each of the individual detectors measuring $P_{probe-inc}$, $P_{pump-inc}$, and $\Delta P_{probe-refl}$ may be combined with $A_{effective}$ and f into a single overall system calibration constant C. Therefore in terms of a calibration factor C, Eq. 4 could be expressed as:

$$\Delta V_{probe-refl} = C\ V_{probe-inc} \Delta R_{sim}(t)\ V_{pump-inc}(1-R_{pump}) \quad (6),$$

where $\Delta V_{probe-refl}$ is the output voltage from the detector used to measure the change in the power of the reflected probe light (D1), $V_{pump-inc}$ is the output voltage from the detector used to measure the incident pump light (D4), and $V_{probe-inc}$ is the output voltage of the detector used to measure the incident probe light (D2). Thus, it is sufficient to determine the constant C. This can be accomplished by either of the following two methods.

(a) A first method measures the transient response $\Delta V_{probe-refl}$ for a sample in which all of the quantities are known which enter into the calculation of the simulated reflectivity change $\Delta R_{sim}(t)$ of the sample, when it is illuminated with a pump pulse of unit energy per unit area of the sample. Next, the method measures $V_{probe-inc}$ and $V_{probe-inc}$, then determines $R_{pump}$ either by measurement or from the computer simulation. The method then finds the value of the constant C such that Eq. 6 is satisfied.

(b) A second method measures the transient response $\Delta V_{probe-refl}$ for a reference sample for which the transient optical response $\Delta R(t)$, when it is illuminated with a pump pulse of unit energy per unit area of the sample, has been measured using a system which has been previously calibrated, for example, by one or more of the methods described above. The method then measures $V_{probe-inc}$ and $V_{pump-inc}$ determines $R_{pump}$ by measurement, and then finds the value of the constant C such that the following equation is satisfied:

$$\Delta V_{probe-refl} = C\ V_{probe-inc} \Delta R(t) V_{pump-inc}\ (1-R_{pump}) \quad (7)$$

For both of these methods it is desirable to establish the autofocus conditions prior to making measurements of $\Delta V_{probe-refl}$, since C depends on the value of $A_{effective}$.

Figure 6A:
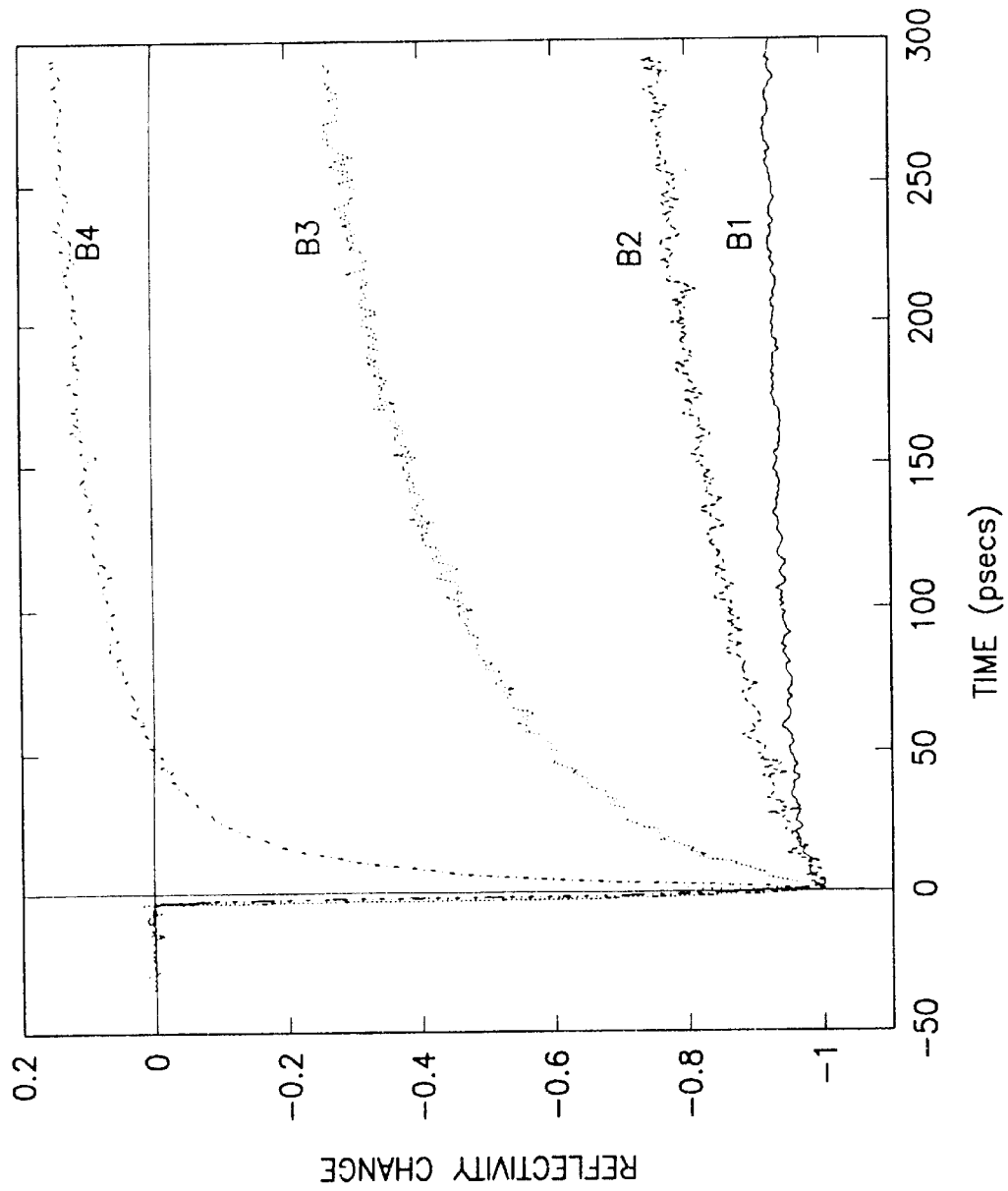
FIG. 6A is a graph illustrating a change in reflectivity over 300 picoseconds for four semiconductor samples each having different implant densities.
Figure 6B:
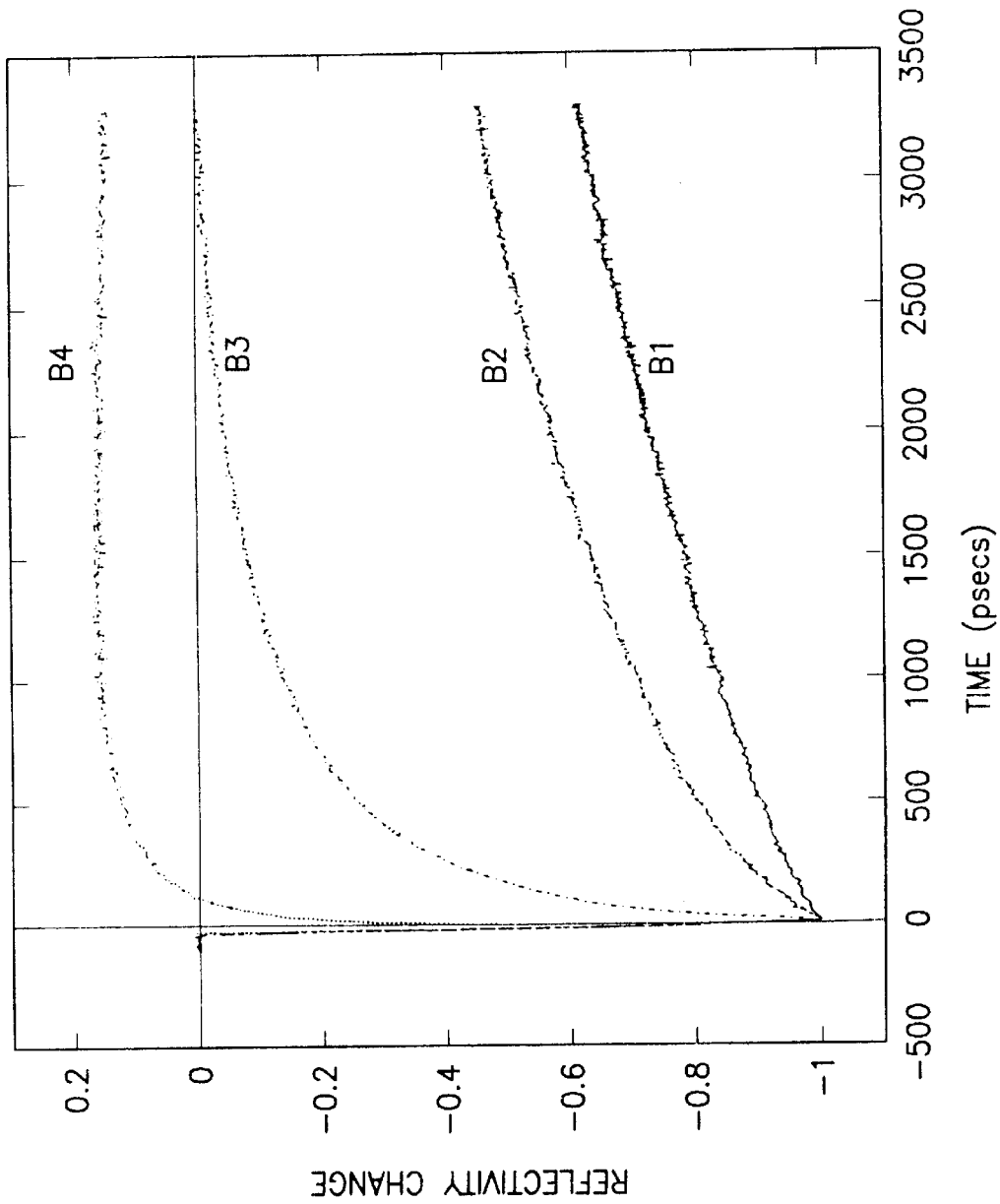
FIG. 6B is a graph illustrating the change in reflectivity over 3500 picoseconds for the four samples of FIG. 6A.

The graphs of FIGS. 6A–6B illustrate data that was obtained from four boron-implanted wafers (designed B1–B4). Each graph plots the change $\Delta R(t)$ in optical reflectivity as a function of time after the pump pulse has been absorbed in the sample ($t_0$ in FIGS. 7A and 7F). The implant energy was 40 keV for each wafer, and the dosages are shown in Table 1.

TABLE 1

| SAMPLE # | DOSE (cm$^{-2}$) |
|---|---|
| B1 | 0 |
| B2 | $5 \times 10^{10}$ |
| B3 | $5 \times 10^{11}$ |
| B4 | $5 \times 10^{12}$ |

Figure 4:
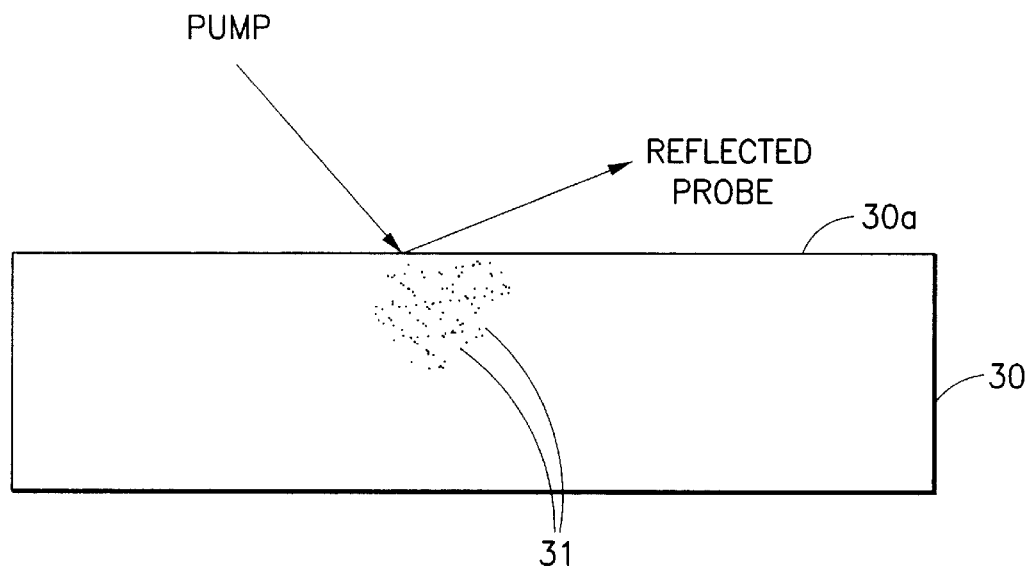
FIG. 4 is an enlarged cross-sectional view, not to scale, of a portion of a semiconductor wafer having an ion implanted region.

FIG. 4 illustrates the sample 30, comprised of a semiconductor material such as silicon, having an implanted region that underlies the surface 30a. The implanted region is comprised of implanted atoms and defect sites, shown collectively as 31. The depth of the implant region is a function of, among other factors, the mass of the implanted ion, the crystalline characteristics of the sample material, which may include overlying layers, and the implant energy.

The graphs of FIGS. 6A and 6B present data which show that the recovery rate of the semiconductor material, after excitation, increases monotonically with increasing dosage and with increasing implant energy. The largest change in reflectivity occurs within the first few picoseconds after the application of the pump pulse.

A preferred procedure to obtain a most accurate estimate of implant dosage for an unknown test sample is as follows. First, $\Delta R(t)$ data is taken for some number of known test samples with implant levels in a range that includes the dosage level of the test sample, e.g., between $10^{10}$ cm$^{-2}$ and $5 \times 10^{10}$ cm$^{-2}$. This reference data may be stored in a data storage device. Second, an interpolation is performed between the different known samples to find estimated curves of $\Delta R(t)$ for intermediate implant doses. Third, a comparison is made between the interpolated curves and the curve(s) obtained from an unknown sample to determine the implant dose of the unknown sample.

It should be noted that it is not required to measure the entire curve of ΔR(t) as a function of time. One can a instead measure ΔR(t) at some predetermined number (e.g., three) of suitably selected times, and to carry out the analysis based on the results obtained at the selected times. By example only, and referring to FIG. 6B, it may be desirable to determine ΔR(t) only at times of 50, 100 and 150 psec, or at times of 50, 250 and 500 psec, and to interpolate the ΔR(t) curve shape from the measured points.

Data for a number of other implant species including As, Ge, Si, $BF_2$, H and P have also been obtained. In general, the forms of the curves of ΔR(t) are qualitatively similar to the results for boron as shown in FIGS. 6A–6B.

Figure 10A:
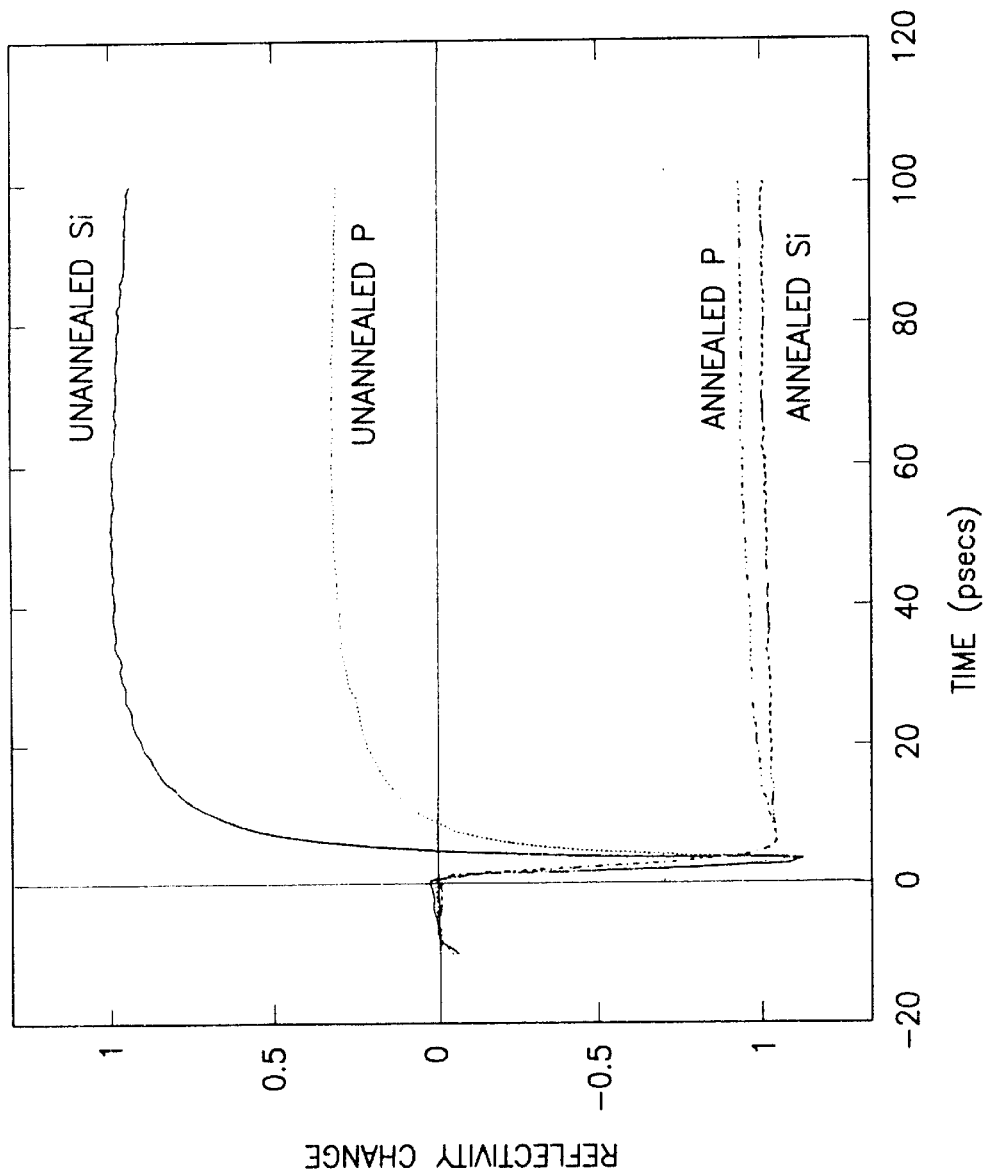
FIG. 10A is a graph illustrating a change in reflectivity over 100 picoseconds for wafers implanted with Si and P ions, before and after thermal annealing to reduce the damage caused by the implantation process.

By example, the top ΔR(t) curves in FIG. 10A illustrate data obtained with Si and P ions implanted into the surface 30a of a silicon sample 30. The dose was $10^{14}$ cm$^{-2}$ and the implant energy was 30 kev. The lower two curves show data taken for the same samples after annealing at 950° C. for 30 minutes. These measurements show that the invention can be used as a test to confirm that annealing of implant damage has been achieved.

Figure 10B:
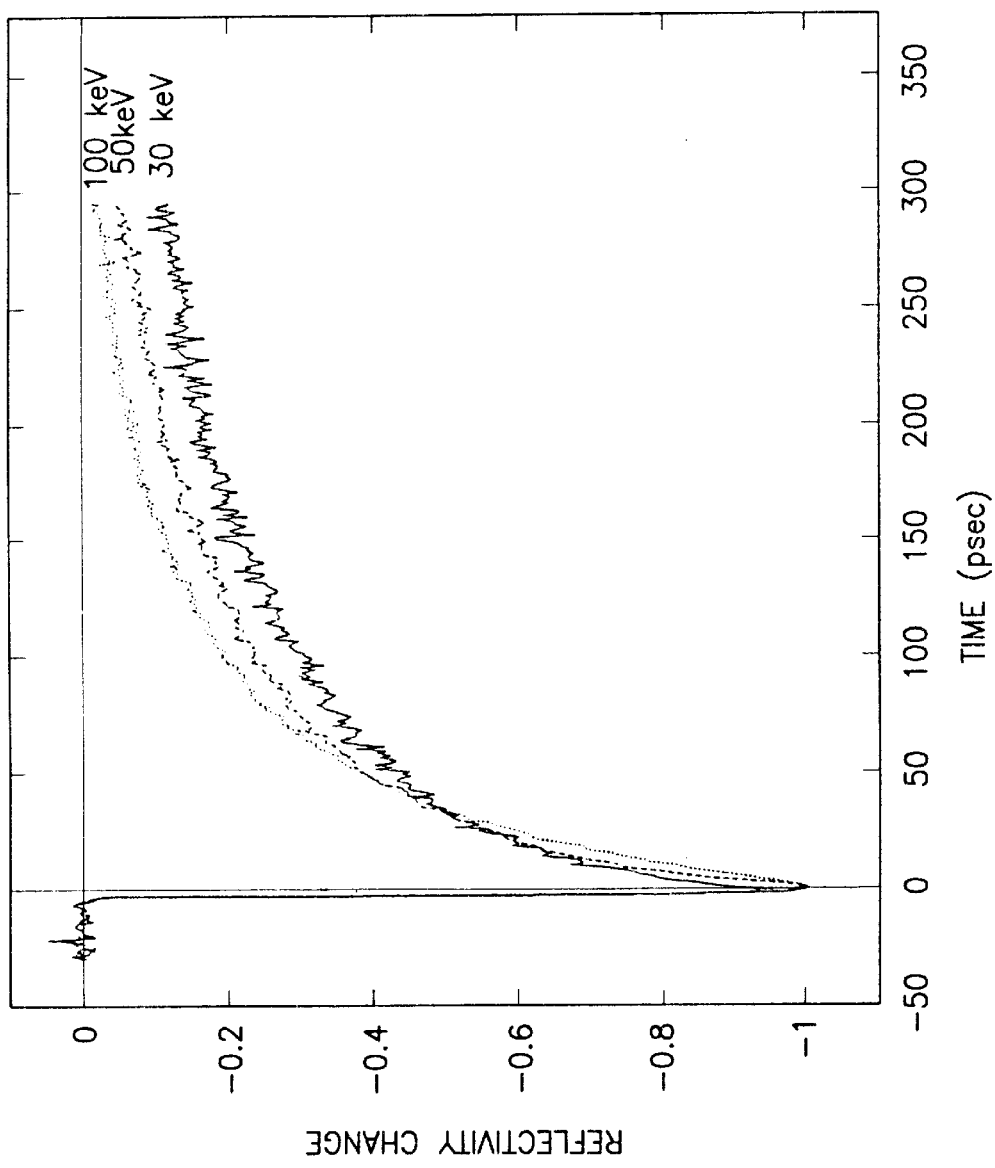
FIG. 10B is a graph illustrating a change in reflectivity over 300 picoseconds for three silicon wafers each implanted with the same dose of boron atoms but with different implant energies.

FIG. 10B illustrates an aspect of the invention wherein the implant energy can be determined from the measurement of ΔR(t). Measurements are shown for three silicon wafers implanted with B ions at a density of $10^{12}$ cm$^{-2}$. The samples were implanted at ion energies of 30, 50 and 100 keV as indicated in the figure. It should be noted that these three data sets have each been independently scaled so that the maximum change in reflectivity is normalized to have unit magnitude.

Figure 10C:
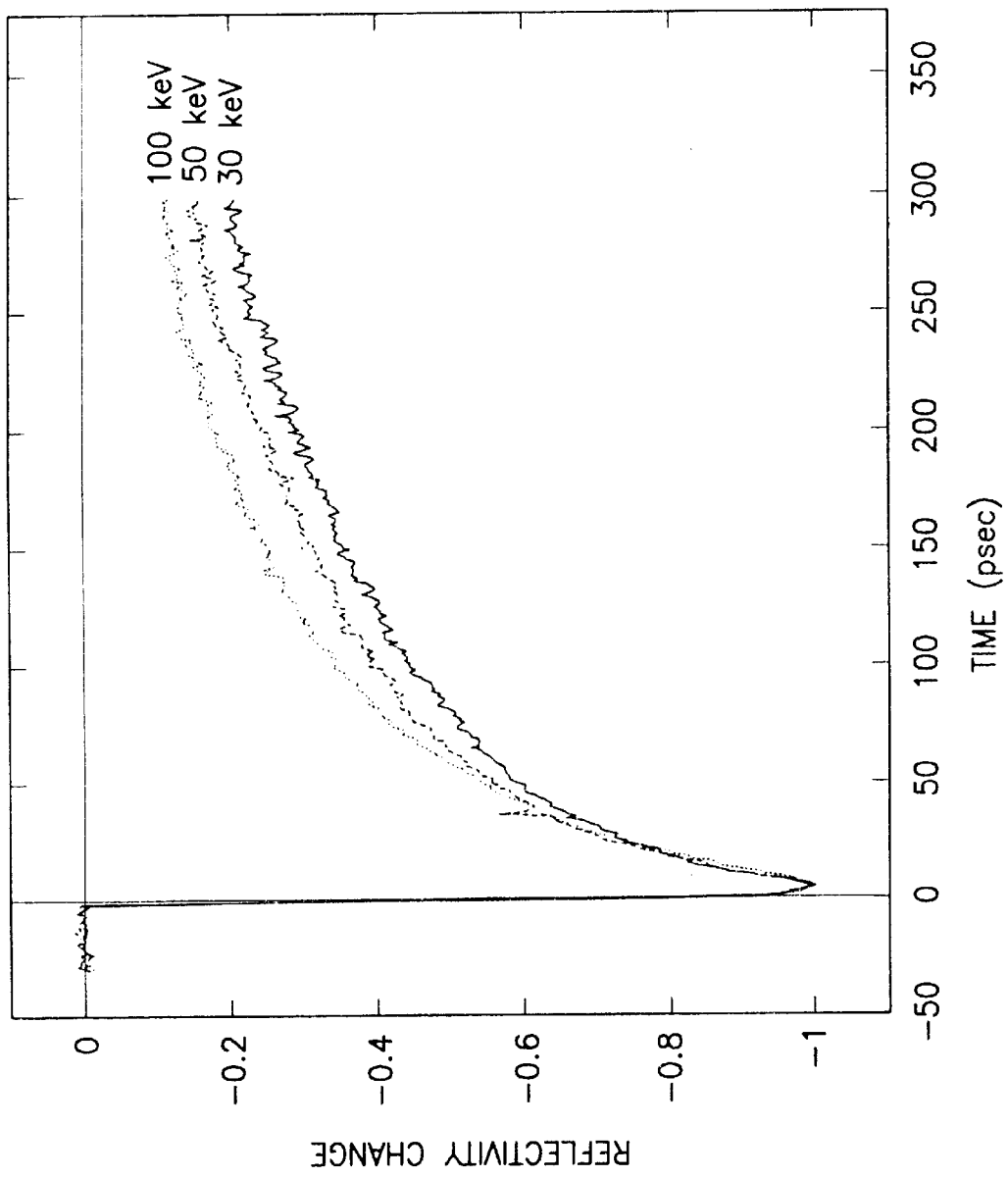
FIG. 10C is a graph illustrating a change in reflectivity over 300 picoseconds for three silicon wafers each with an overlayer of silicon dioxide, and implanted with the same dose of boron atoms but with different implant energies.

FIG. 10C illustrates an aspect of the invention wherein the implant dose can be determined through an overlying layer that does not significantly absorb the pump or probe beams. Measurements are shown for three silicon wafers implanted with B ions at a density of $10^{12}$ cm$^{-2}$. The samples were implanted at ion energies of 30, 50 and 100 keV as indicated in the figure. Each silicon sample was coated with a layer of dielectric material, specifically $SiO_2$, having a nominal thickness of approximately 220 Angstroms. As is evident, the measurement system in accordance with the teaching of this invention is capable of characterizing the implant dose through an overlying film or layer of material that does not strongly absorb the wavelength(s) of interest (e.g., a wavelength in the range of 700 to 800 nm in the present instance).

Figure 10D:
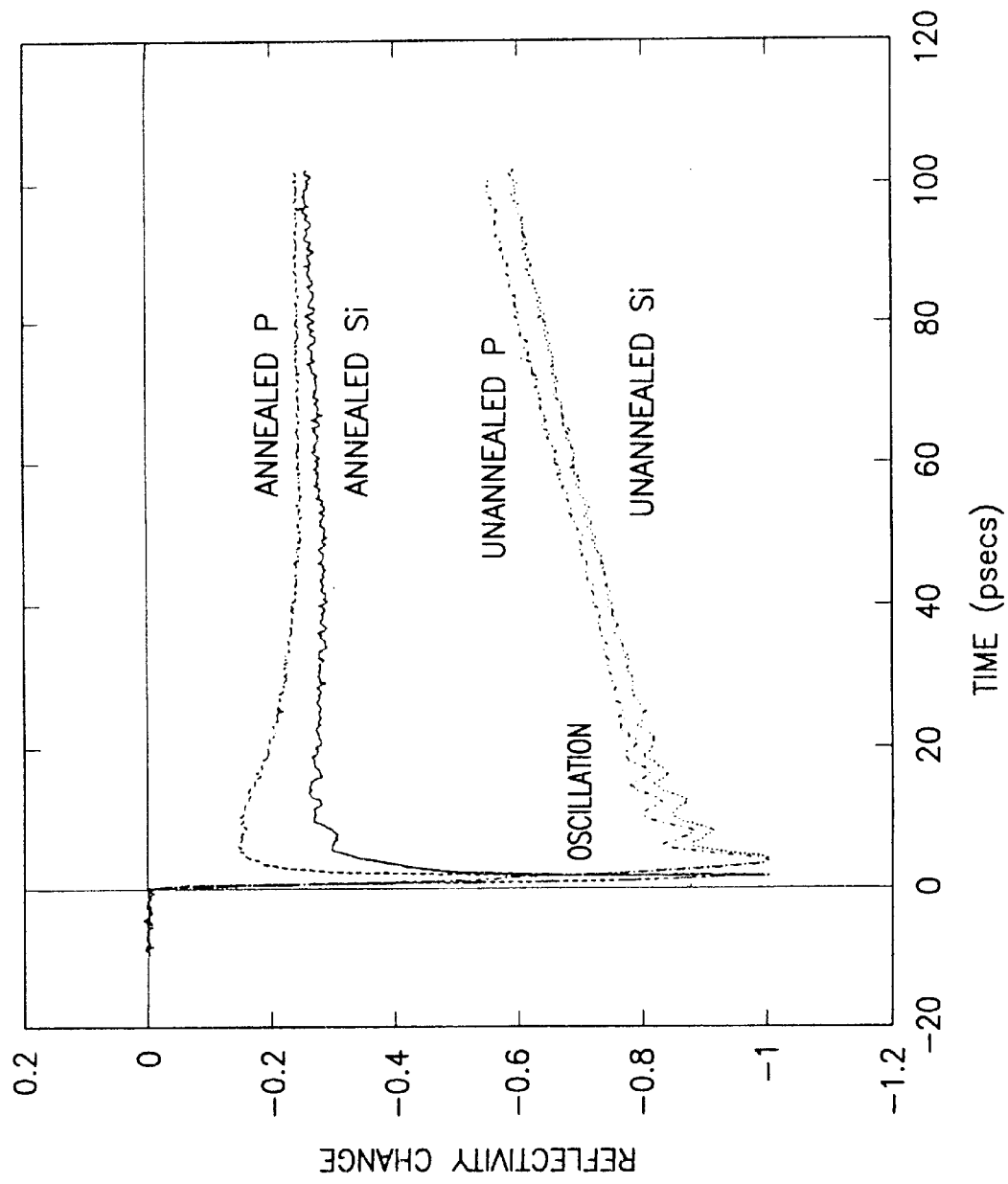
FIG. 10D is a graph illustrating a change in reflectivity over 100 picoseconds for wafers implanted with si and P ions, before and after thermal annealing to reduce the damage caused by the implantation process, wherein the wafers studied are the same as in FIG. 10A, but the wavelengths of the pump and probe beams are reduced by a factor of approximately two; wherein in FIGS. 6A, 6B and 10A–10D the quantity plotted in the vertical direction is the reflectivity on a scale such that the maximum change is one unit.

FIG. 10A shows results obtained with the pump and the probe light having a wavelength in the range of around 750 nm. FIG. 10D illustrates data obtained from the same wafers through the use of pump and probe light of wavelength around 400 nm. In this wavelength range the optical absorption is considerably larger. The high absorption of light in the layer near the surface sets up a stress which causes a mechanical wave to be launched into the structure. As this wave propagates away from the surface it produces a local modification of the optical properties of the wafer. The probe light pulse undergoes partial reflection at the instantaneous location of the mechanical wave. The interference between the part of the probe light pulse reflected at the mechanical wave and the part of the probe light reflected at the surface of the wafer gives rise to the oscillations in ΔR(t) which can be seen in FIG. 10D. In the annealed wafers the optical absorption in the implanted region near to the wafer surface is not as large. Consequently, a weaker mechanical wave is generated and the oscillations in ΔR(t) are smaller. Thus, the determination of the strength of the oscillations provides another means to evaluate the condition of the ion-implanted layer near the surface of the wafer.

It is possible that the results for ΔR(t) for a given implant dose and energy may be affected to some extent by several other parameters. These may include the beam current per unit area during the implant process, the doping of the semiconductor material (if any), other features of the surface preparation, and the intensity of the laser pulses used for the measurement. If this is the case then it is desirable that the known samples also be prepared and/or characterized in the same or a similar manner as the unknown samples.

Figure 7A:
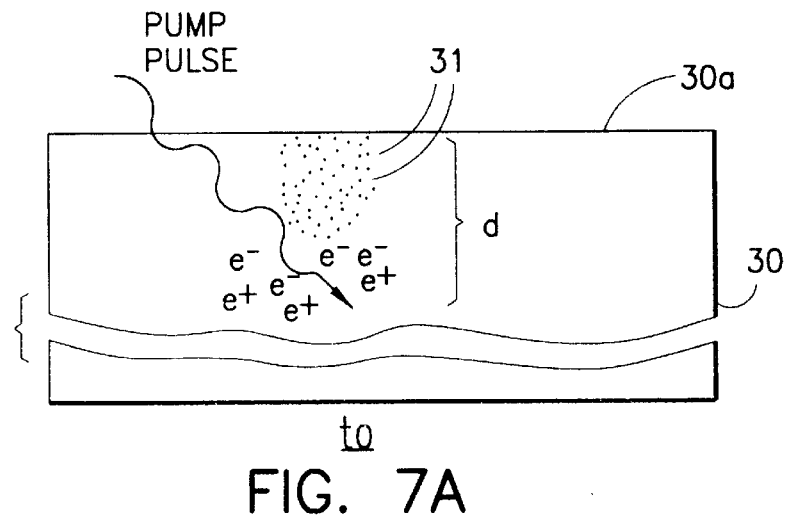
FIGS. 7A–7E are enlarged cross-sectional views, not to scale, showing the generation of charge carriers by the pump beam at time $t_0$ (FIG. 7A), the diffusion of the charge carriers at time $t_1$ (FIG. 7B), and the application of probe beams at times $t_2$ and $t_3$.

Referring to FIGS. 7A–7E, it is believed that the observed effects can be understood as follows. As is shown in FIG. 7A, a fraction of the pump pulse is absorbed in the implant region and the remainder is absorbed in the sample 30. The absorption length (d) in the sample depends on wavelength. For the wavelength range of 700 nm to 750 nm the absorption length is typically 7 micrometers for a silicon sample. The absorption of the pump pulse results in the generation of charge carriers, i.e., electrons (e$^-$) and holes (e$^+$) are generated throughout the absorption length distance. The free electrons and holes affect the optical "constants" of the semiconductor sample and result in a change in reflectivity.

Figure 7B:
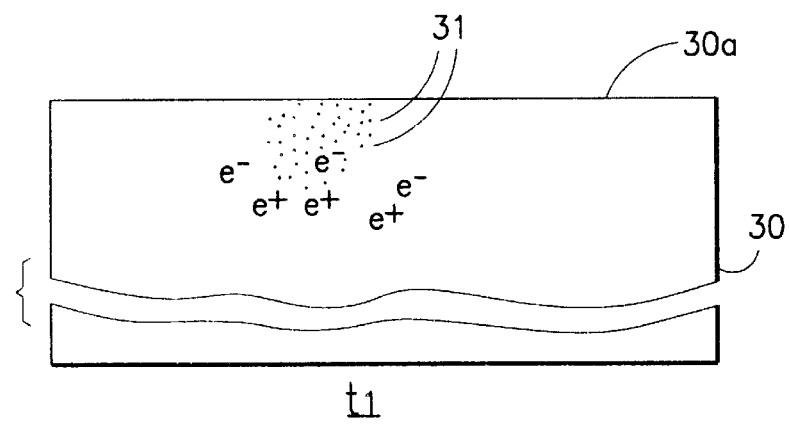

In an ion-implanted sample there is rapid recombination of the charge carriers at or near the surface 30a. FIG. 7B shows the diffusion of the charge carriers into the implanted region and into the surrounding non-implanted region of the sample. The rate at which the excited carriers are removed is determined by the rate of the surface recombination, together with the diffusion coefficients of electrons and holes in the semiconductor material. Within the implanted region the removal of the charge carriers due to recombination and trapping at defect sites will differ significantly from what occurs in the non-implanted semiconductor material.

Thus, and unlike in the report of F. E. Doany et al. referred to above, in which a thin film of a semiconducting material was studied, the charge carriers must diffuse before they can interact with the implanted ions and defects near the material's surface.

Figure 7C:
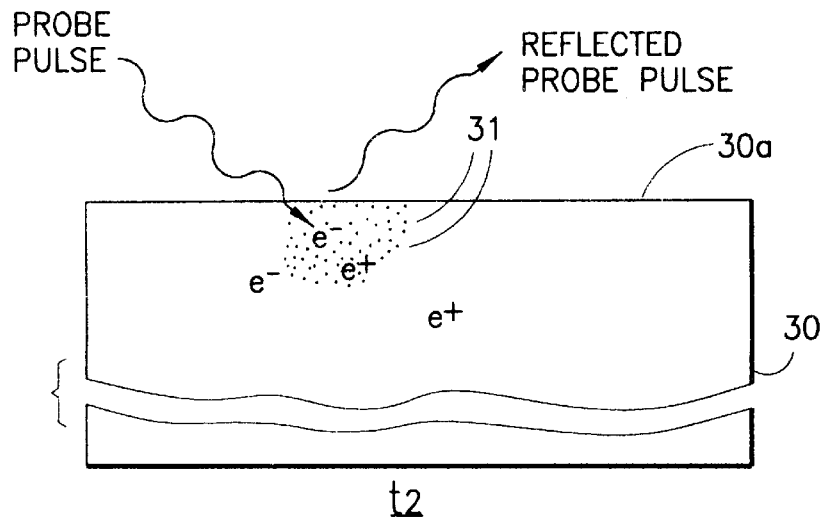
Figure 7D:
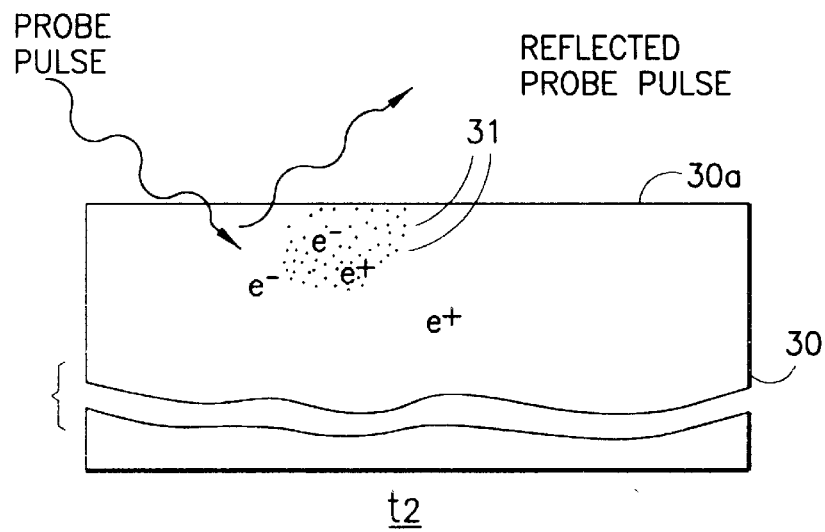
Figure 7E:
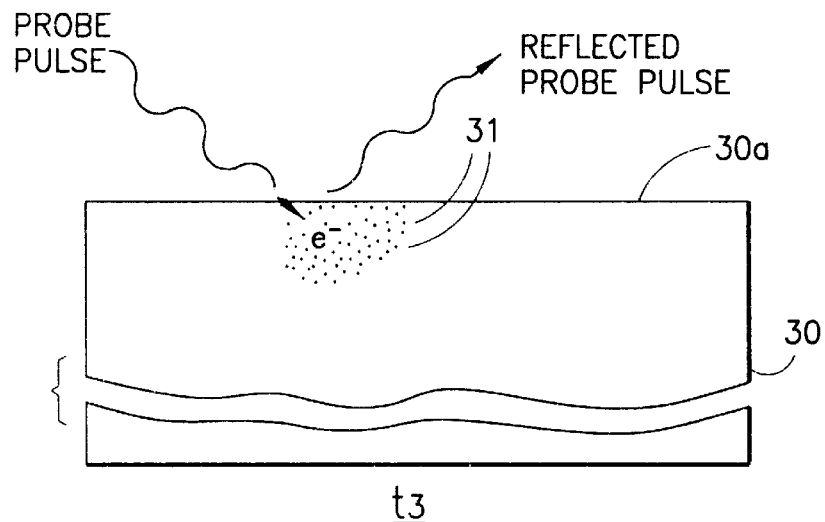
Figure 7F:
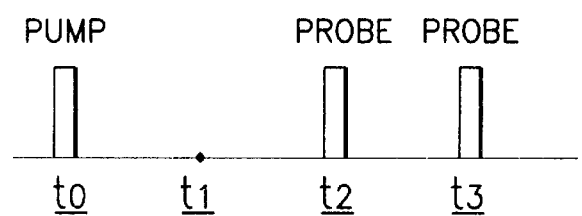
FIG. 7F is a timing diagram that relates to the sequence shown in FIGS. 7A–7E, wherein each probe pulse has a distinct pump pulse at $t_0$.

FIG. 7C illustrates a first probe pulse that arrives at time $t_2$, for example 10 picoseconds after the arrival of the pump pulse ($t_0$), and that strikes the implanted region. FIG. 7D also illustrates the first probe pulse that arrives at time $t_2$, but that strikes the non-implanted region. For this case it is clear that optical properties of the implanted and the non-implanted regions will differ, and that the resulting change in optical reflectivity of the sample to the probe beam will also differ. FIG. 7E illustrates a second probe pulse that arrives at time $t_3$, for example 20 picoseconds after the arrival of the pump pulse ($t_0$), and that strikes the implanted region. Contrasting FIGS. 7C and 7E, it can be seen that during the additional 10 picoseconds that elapse from the absorption of the pump pulse that fewer charge carriers will remain within the implanted region. The reduction in the number of charge carriers results in a corresponding, and measurable, change in the optical constants of the sample and, for example, in a time-dependent change in the reflectivity of the sample 30 to the probe beam.

This invention exploits the above-described mechanisms to measure a change in reflection, polarization, phase, etc. due to a change in optical constants over time, and to correlate this change with at least one of implant dosage, implant energy, dopant species type, the presence or absence of an implanted chemical species within a region of a sample, a level of implant-related damage, and other effects relating to the introduction of a chemical species into a sample.

FIG. 9 makes it clear that the pump and probe pulses may be applied in pairs. That is, for each pump pulse a single probe pulse is applied to the sample to measure the change in reflectivity. By example, for a series of pump pulses each of which is defined to be applied at time $t_0$, a corresponding probe pulse is applied at different time delays ($t_D$) of $t_1$, $t_2$, $t_3$, and $t_{max}$. The spacing between pump pulses (e.g., 1/75 MHz or 13.3 nanoseconds) insures that the optical effects resulting from the previous pump pulse have become small before the application of the next pump pulse.

It is also within the scope of this invention to apply a single pump pulse, followed by two or more probe pulses. It is also within the scope of this invention to apply one or more pump pulses, and a cw or substantially cw probe beam.

It should also be apparent from FIG. 9 that this invention enables a characterization of an implanted or diffused region in a very short period of time. That is, and assuming that three probe pulses are used and that the resulting reflectivity measurements used to interpolate the $\Delta R(t)$ curve, an entire measurement cycle can be concluded in approximately 40 nanoseconds, or the time required to generate three consecutive pump pulses (and corresponding probe pulses) at a 75 MHz rate. However, so as to compensate for variations in the probe and pump optical pulses, a series of measurements are preferably taken over a longer period of time and then averaged to improve the signal-to-noise ratio.

It is within the scope of this invention to vary the wavelength of the pump and/or probe pulses during a measurement cycle, and to use other wavelengths than those in the range of 700 nm to 750 nm. A change in $\lambda$ may also reduce the data acquisition time considerably. Similarly, a reduction in the spot size on the surface 30a should also reduce the measurement time.

It is also within the scope of this invention to generate a sequence of pump pulses at a first frequency ($f_1$) and a sequence of probe pulses at a second frequency ($f_2$), wherein $f_2 \neq f_1$. In this case a signal averager can be triggered at a rate that is equal to $f_1 - f_2$.

In addition, the teaching of this invention is applicable to a number of different types of sample materials other than Si, including, but not limited to, Ge, the Group III-V alloy materials (e.g., GaAs, GaAlAs), and also Group II-VI alloy materials. The teaching of this invention is also not limited for use only with the specific chemical species that have been described above. Furthermore, the measurement system in accordance with the teaching of this invention is also well suited for measuring samples into which a chemical species has been diffused from a solid, liquid or gaseous source, and wherein an amount of physical damage to the sample may be negligible.

In still other embodiments of this invention the wavelength of the pump and/or probe pulsed beams can be selected or tuned to an energy level of the chemical species that has been introduced into the sample, or may be tuned to an energy transition of the sample itself, thereby enhancing sensitivity and desensitizing the measurement to surface effects.

In still other embodiments of this invention, and assuming that a photodetector having an adequate response time is available, the probe pulse can be eliminated and the photodetector used to measure a change in the optical constants of the sample that occurs during the pump pulse itself.

It should be clear that the teaching of this invention overcomes the problems inherent in the optical measurement systems that were referred to earlier. By example, the measurement system of this invention operates in the time domain and not in the frequency domain. By examining the sample over very short time scales only transient effects are considered. Even though a background equilibrium population of charge carriers may be generated over a series of pump pulses, the system of this invention examines only the transient effect induced by a most recent pump pulse, and is not specifically concerned with the dynamics of the background equilibrium population.

Furthermore, the acoustic techniques of, by example, Tauc et al. can be employed as an adjunct to the measurement system in accordance with this invention. By example, the acoustic technique can be employed to measure the depth of an implanted region, while the measurement technique of this invention can be employed to determine the density of the implanted species.

By a further example, the top $\Delta R(t)$ curves in FIG. 10D illustrate data obtained with Si and P ions implanted into the source 30a of a silicon sample 30. The dose was $10^{14}$ cm$^{-2}$ and the implant energy was 30 keV. The lower two curves show data taken for the same samples after annealing at 950° C. for 30 minutes. These measurements were made using pump and probe light pulses of wavelength 400 nm. As was described previously, at this short wavelength the light is strongly absorbed in a layer near to the surface and a stress is set up in this region. This stress launches a strain pulse into the interior of the wafer. This strain causes a local change in the optical properties of the silicon. When the probe light pulse passes through the region containing the strain pulse it is partially reflected. The interference between this reflected component of the probe light and the part of the probe light reflected at the surface of the silicon wafer gives rise to the oscillations in optical reflectivity which can be seen in FIG. 10D. The magnitude and also the frequency of these oscillations can be used as a probe of the ion density and of the extent to which the damage has been annealed.

It should further be realized that while the wavelength of the pump radiation should be suitable for generating electrons and holes in the semiconductor sample, the wavelength of the probe radiation is not so constrained.

An important aspect of this invention is that measurements are made on a very short time scale, typically less than one nanosecond. Because of this very short time scale the carriers injected by the pump light pulse are moving in the surface region of the sample where the surface electric field and the surface doping have an important effect. Measurements on longer time scales would not be able to give the type of information that can be obtained through the use of the present invention.

Several examples of applications to which the teaching of this invention can be employed to advantage will now be given.

One application of interest is that of a semiconductor sample in which a p-n junction has been formed by doping, for example, via diffusion or implantation. In this case the magnitude and direction of the electric field in the region of the junction depends on the detailed distribution of electrically active impurities in the sample. The behavior of electrical carriers injected by an optical pump pulse while in the vicinity of the junction is subject to the dopant distribution and its associated electric field in a calculable manner. From a suitable model of the junction the temporal behavior of the injected carriers and the effects of these carriers on the optical reflectivity of the sample, as they move in the electric field, may be calculated. Likewise, the dopant concentration and distribution within the sample may be represented in terms of certain parameters, for example, the dopant concentration on each side of the junction, the metallurgical width of the junction, and the permittivity of the semiconductor, and these parameters may be adjusted within the model to obtain a simulation in best agreement with measured optical reflectivity data over a suitable time period. In this way the p-n junction may be characterized by the ultra-fast optical system of this invention.

Another application of interest is that of an implanted sample containing residual implant damage and having a surface charge, possibly as a result of electrically charged defects caused by the implantation process. To model the picosecond reflectivity change in such a sample, and subsequently to adjust the parameters of the model in order to bring it into agreement with a measurement, it is necessary to include sample parameters which account for the surface electric field within the sample, as well as the electrical doping concentration, ambipolar diffusion, and recombination rates for electrons and holes.

Another application of interest is that of a sample which has negligible implant damage, for example, it may have been annealed, or it may not have been doped, or it may have been doped by means other than implantation, but has a surface oxide which contains a concentration of electrical charge which may be unknown. In this case, the ambipolar diffusion rate in the sample will be substantially like that in non-implanted material, and the behavior of photocarriers injected by the pump pulse will be dominated by the electrical field due to the electrically charged surface oxide layer. The electric field also depends on the doping concentration in the semiconductor which may be unknown. Since it is possible to calculate the electrical field in the sample taking all such factors into account, and it is also possible to calculate the motion of the photoinjected carriers in this field, it is possible to measure the doping concentration and surface oxide charge by adjusting suitable parameters in a model of such a sample in order to obtain agreement with a picosecond transient reflectivity measurement.

Methods for calculating the electric fields within a semiconductor due to dopant gradients and surface charges are well-known in the art. References in this regard are S. M. Sze, "Physics of Semiconductor Devices", New York: John Wiley and Sons, 1969, and also A. S. Grove "Physics and Technology of Semiconductor Devices", New York, John Wiley and Sons, 1967.

A further application of interest is that of a semiconductor sample which may have little or no damage, but which may contain dopants and possibly also other impurities which are not, however, considered dopants because they introduce so-called deep level traps in the semiconductor material. The semiconductor may also have surface electrical charges as in the previous case which give rise to an electric field. The deep level traps provide a mechanism for the photocarriers injected by the pump pulse to recombine. The rate at which recombination occurs may be characterized by a minority carrier lifetime, or alternatively by a surface recombination velocity. Thus by making a measurement of the picosecond transient decay of the reflectivity of the sample, and relating this to the population and distribution of injected carriers, the minority carrier lifetime or surface recombination velocity may be determined. Further, since these parameters depend on the amount of an impurity in a semiconductor wafer, the measured lifetime or recombination velocity may be related to an impurity concentration.

All of the examples listed above can be influenced by an applied electric field, by optical illumination, or by a change in the temperature of the sample. In accordance with an aspect of this invention, measurements made as a function of one or more of these parameters allow a more comprehensive measurement of the sample properties, e.g., surface charge, dopant concentration, trap density, and minority carrier lifetime. In one aspect, therefore, the teaching of this invention enables a charge carrier related characteristic of a semiconductor material (such as carrier lifetime, mobility, etc.) to be determined.

It is also within the scope of the teaching of this invention to apply an external electric field to the sample, which in turn leads to a change in the time-dependence of the carrier distribution. An analysis of this change can give further information about the quantities that are to be determined. The electric field may be applied by one or more of the following methods.

Figure 8A:
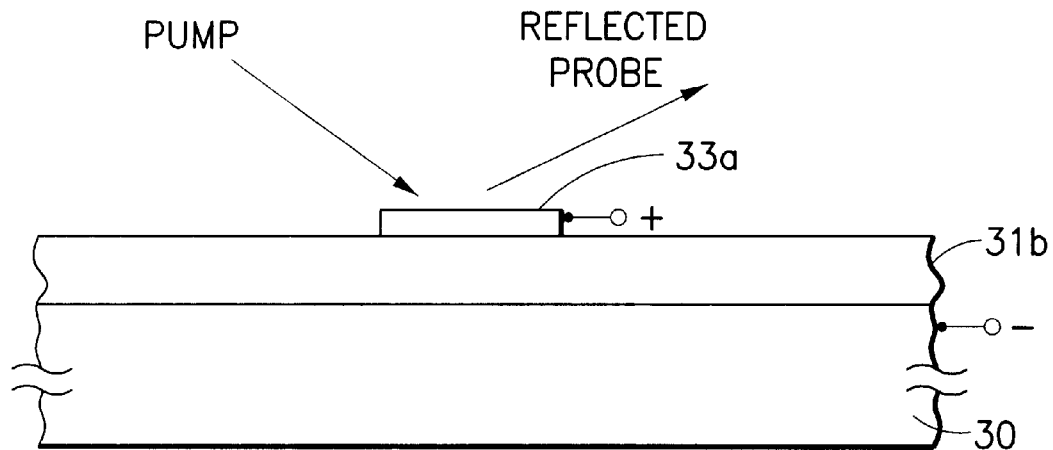
FIG. 8A is a cross-sectional area of a semiconductor sample showing a transparent electrode that is deposited on the sample.

Referring to FIG. 8A, in a first method a semi-transparent electrode 33$a$ is deposited on top of the sample, the electrode 33$a$ having an area at least the size of the focused pump and probe beams. In this embodiment the semiconductor sample may include an oxide or other dielectric layer 31$b$ that may or may not include charge carriers.

In a second method the semi-transparent electrode 33$a$ is provided in close contact with the surface of the sample, but is not actually fabricated on the sample. By example, the electrode is fabricated on another (transparent) substrate, and is then contacted to surface of the sample.

Figure 8B:
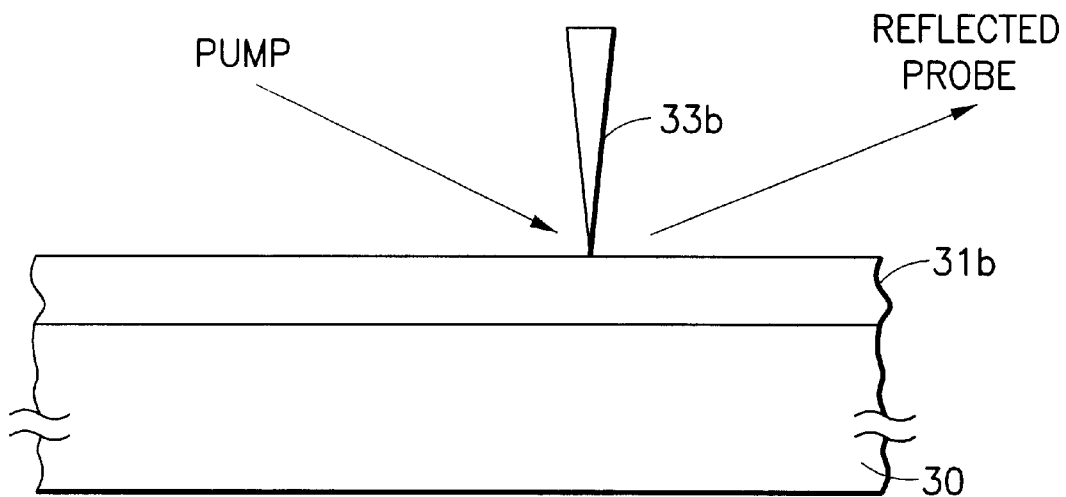
FIG. 8B is a cross-section view of a semiconductor sample showing an external electrode that is contacted to the sample.

Referring to FIG. 8B, in a third method an electrode 33$b$ with a tapered tip is held in close proximity with the surface of the sample in order to induce a known amount of charge on the surface of an insulating layer.

When an externally applied electric field is used, several different procedures for making measurements are within the scope of this invention. These include, but are not necessarily limited to, the following.

(1) $\Delta R$ (t) is measured for a fixed time delay time t between the pump and the probe while the applied field is varied over a suitable range.

(2) $\Delta R$ (t) is measured for a fixed delay time t while the applied electric field is modulated by a small amount $\Delta E$ about a constant average value $E_o$. Thus the derivative d $\Delta R(t)/dE$ is measured.

(3) $\Delta R(t)$ is measured as a function of the time t for two different applied electric fields $E_1$ and $E_2$.

Other measurement schemes may be apparent to those skilled in the art, based on the foregoing disclosed techniques.

A change in the intensity of the pump beam changes the number of carriers excited in the sample. For each intensity of the pump beam the transient change in the optical reflectivity $\Delta R(t)$ may have a different functional form. By example, for two different pump intensities $I_1$ and $I_2$ the measured changes in reflectivity are $\Delta R_1(t)$ and $\Delta R_2(t)$, respectively. Then, the ratio of $\Delta R_1(t)$ to $\Delta R_2(t)$ depends on the particular time t that is considered, i.e. $\Delta R_1(t)$ and $\Delta R_2(t)$ do not satisfy the relation $\Delta R_1(t)=c \Delta R_2(t)$ with c a constant independent of time. Thus, it can be advantageous to further characterize a sample through measurement of $\Delta R(t)$ as a function of the intensity, or wavelength, or wavelength distribution, of such illumination.

A change in temperature of the sample modifies the number of carriers present before the application of the pump pulse, and will also change the rate at which carriers are trapped. Consequently, $\Delta R(t)$ is modified by such a change in sample temperature. Thus, it is possible under certain conditions to make measurements as a function of temperature, or to make all measurements at one specified temperature. This technique enables measurements to be made under conditions such that the results are most sensitive to a particular attribute of greatest interest (for example, surface charge, dopant concentration, trap density, or minority carrier lifetime).

In a further embodiment of this invention the pump and probe pulses are directed to different locations on the surface of the sample. This can be accomplished by applying each set of pulses through different optical fibers, as illustrated in FIG. 3A, possibly using the reduced tip diameter embodiment of FIG. 3B. The absorption of the pump pulses leads to the generation of charge carriers in the semiconductor material, as described above. By so directing the pump and probe pulses the system of this invention can be used to measure characteristics of the motion, such as mobility, of the charge carriers in the direction parallel to the surface of the sample. During the measurement an electric field can be applied, and/or the temperature can be varied, and/or the sample can be exposed to illumination, as described above.

Further in accordance with the teachings of this invention there is described a method for characterizing a sample that includes the following steps. A first step provides a database of stored data obtained from a plurality of reference samples. The data for each of the plurality of reference samples is generated in response to absorbing a pump light pulse in a portion of the semiconductor material of each sample and measuring a change in optical constants as indicated by a probe light pulse applied at some time t following the absorption of the pump light pulse. A next step provides a semiconductor material sample to be characterized, followed by a step of absorbing pump light pulses in a portion of the semiconductor material being characterized for generating charge carriers within the semiconductor material. A next step measures changes that occur in optical constants as indicated by probe light pulses applied at some time t following the absorption of the pump light pulses. This method then performs a step of comparing the measured changes with the stored data and associating measured changes in the optical constants with at least one of a surface charge, dopant concentration, trap density, or minority carrier lifetime, in accordance with a reference sample having stored data that most closely matches the measured changes observed in the semiconductor material sample being characterized.

The teaching of this invention has thus been described in the context of apparatus and methods for inducing at least one transient time-dependent change in the optical constants n and κ of a sample in a region close to the surface of the sample, and possibly also in a displacement of the surface. These changes lead to a change ΔR(t) in the optical reflectivity, a shift δϕ(t) in the phase of the reflected or transmitted light, a change in the polarization state of the reflected light, and a change in direction of the reflected or transmitted light. These changes are dependent also on the polarization and the angle of incident of the probe light. The measured changes in the response of the sample to light depend, among other things, on the distribution of defects and foreign atom species near the sample's surface and in the bulk. The measured changes are associated with at least one of species concentration, species type, implant energy, the presence or absence of an introduced-species region within the location, a presence or absence of implant-related damage, and a presence or absence of an electric field.

Thus, while the invention has been particularly shown and described with respect to preferred embodiments thereof, it will be understood by those skilled in the art that changes in form and details may be made therein without departing from the scope and spirit of the invention.

What is claimed is:

1. A method for characterizing a sample, comprising the steps of:
    providing a semiconductor material;
    applying an electric field to the semiconductor material;
    absorbing a pump light pulse in a portion of the semiconductor material and measuring a change in optical constants as indicated by a probe light pulse applied at some time t following the absorption of the pump light pulse; and
    associating a measured change in the optical constants with at least one of a surface charge, dopant concentration, trap density, or minority carrier lifetime.

2. A method as set forth in claim 1, wherein the step of applying an electric field includes a step of applying the electric field from an electrode disposed over a surface of the semiconductor material.

3. A method as set forth in claim 1, wherein the step of applying an electric field includes a step of applying the electric field from an electrode disposed upon a surface of the semiconductor material.

4. A method as set forth in claim 1, wherein the pump light pulse has a duration of between about 0.01 to 100 picoseconds.

5. A method as set forth in claim 1, wherein the probe light pulse has a duration of between about 0.01 to 100 picoseconds.

6. A method for characterizing a sample, comprising the steps of:
    providing a semiconductor material;
    maintaining the semiconductor material at a predetermined temperature;
    absorbing a pump light pulse in a portion of the semiconductor material and measuring a change in optical constants as indicated by a probe light pulse applied at some time t following the absorption of the pump light pulse; and
    associating a measured change in the optical constants with at least one of a surface charge, dopant concentration, trap density, or minority carrier lifetime.

7. A method for characterizing a sample, comprising the steps of:
    providing a semiconductor material;
    applying one of a pulsed or a constant illumination to the semiconductor material;
    absorbing a pump light pulse in a portion of the semiconductor material to excite electrons and holes in the sample, and measuring a change in optical constants as indicated by a probe light pulse applied at some time t following the absorption of the pump light pulse; and
    associating a measured change in the optical constants with at least one of a surface charge, dopant concentration, trap density, or minority carrier lifetime.

8. A method for characterizing a sample, comprising the steps of:
    providing a semiconductor material;
    absorbing pump light pulses in a portion of the semiconductor material to excite electrons and holes in the sample, wherein the pulses have different intensities, and measuring changes that occur in optical constants as indicated by probe light pulses applied at some time t following the absorption of the pump light pulses; and
    associating measured changes in the optical constants with at least one of a surface charge, dopant concentration, trap density, or minority carrier lifetime.

9. A method for characterizing a sample, comprising the steps of:
    providing stored data obtained from a plurality of reference samples, the data for each of the plurality of reference samples being generated in response to absorbing pump light pulses in a portion of the semiconductor material of each sample and measuring a change in optical constants as indicated by probe light pulses applied at some time t following the absorption of the pump light pulses;

providing a semiconductor material sample to be characterized;

absorbing pump light pulses in a portion of the semiconductor material being characterized for generating charge carriers within the semiconductor material;

measuring changes that occur in optical constants as indicated by probe light pulses applied at some time t following the absorption of the pump light pulses;

comparing the measured changes with the stored data; and associating measured changes in the optical constants with at least one of a surface charge, dopant concentration, trap, density, or minority carrier lifetime, in accordance with a reference sample having stored data that most closely matches the measured changes observed in the semiconductor material sample being characterized.

10. A method for characterizing a sample, comprising the steps of:

providing a semiconductor material;

absorbing pump light pulses to a first location on a semiconductor material for generating charge carriers within the semiconductor material;

measuring a change in optical constants as indicated by probe light pulses individual ones of which are applied at some time t following the absorption of an individual one of the pump light pulses, the probe light pulses being applied at a second location on the semiconductor material; and associating a measured change in the optical constants with a motion of the charge carriers within the semiconductor material.

11. A method for characterizing a sample, comprising the steps of:

providing a semiconductor material;

applying an electric field to at least one surface of the semiconductor material;

absorbing pump light pulses to a first location on a semiconductor material for generating charge carriers within the semiconductor material;

measuring at least one of a change $\Delta R(t)$ in an optical reflectivity, a shift $\delta\phi(t)$ in a phase of reflected or transmitted light, a change in a polarization state of reflected light, or a change in direction of reflected or transmitted light, as indicated by probe light pulses individual ones of which are applied at some time t following the absorption of an individual one of the pump light pulses, the probe light pulses being applied at one of the first location or a second location on the semiconductor material; and associating a measured change in at least one of the reflectivity, phase, polarization state, or direction with at least one of a charge mobility, surface charge, dopant concentration, trap density, or minority carrier lifetime of the semiconductor material.

12. A method as set forth in claim 11, wherein the step of applying an electric field includes a step of applying the electric field from an electrode disposed over a surface of the semiconductor material.

13. A method as set forth in claim 11, wherein the step of applying an electric field includes a step of applying the electric field from an electrode disposed upon a surface of the semiconductor material.

14. A method for characterizing a sample, comprising the steps of:

providing a semiconductor material;

applying an electric field to the semiconductor material;

absorbing a pump light pulse in a portion of the semiconductor material and measuring a change in optical constants as indicated by a probe light pulse applied at some time t following the absorption of the pump light pulse; and associating a measured change in the optical constants with at least one of dopant concentration, trap density, or a charge carrier related characteristic of the semiconductor material, wherein the step of applying an electric field includes a step of one of varying the magnitude of the applied electric field over a range of values; modulating the magnitude of the applied electric field about a predetermined value; or applying at different times two or more different magnitude electric fields.

15. A method as set forth in claim 14, wherein the step of applying an electric field further includes a step of applying the electric field from an electrode disposed over a surface of the semiconductor material.

16. A method as set forth in claim 14, wherein the step of applying an electric field further includes a step of applying the electric field from an electrode disposed upon a surface of the semiconductor material.

17. A method for characterizing a sample, comprising the steps of:

providing a sample comprised of semiconductor material;

applying a plurality of pump light pulses to an area on the surface of the sample to generate constructive and destructive in intensity results, thereby causing a variation in a density of charge carriers in said sample due to absorption of the plurality of pump light pulses;

measuring a change in optical constants as indicated by a probe light pulse applied to the area at some time t following the absorption of the pump light pulses; and associating a measured change in the optical constants with at least one of charge magnitude, dopant concentration, trap density, or a charge carrier characteristic of the sample.

18. A method as in claim 17, wherein the steps of applying and measuring each include a step of simultaneously applying an external electric field to the semiconductor material.

19. A method as in claim 17, wherein the steps of applying and measuring each include a step of simultaneously applying illumination to the semiconductor material.

20. A method as in claim 17, wherein the steps of applying and measuring each include a step of simultaneously varying a temperature of the semiconductor material.

21. A system for characterizing a sample, comprising:

a sample stage for supporting, during a measurement, a sample comprised of semiconductor material;

means for generating charge carriers in the semiconductor material, the means for generating charge carriers comprising a first light source for applying a plurality of pump light pulses to a first area on the surface of the sample;

means for applying a plurality of probe light pulses to the first area or a second area different from the first area of the surface of the sample at some time t following the absorption of the pump light pulses;

means for modifying at least one of a temperature, illumination state, or charge state of the sample during the measurement; and at least one detector and a data processor for measuring a change in optical constants of the sample as indicated by the probe light pulses, and for associating a measured change in the optical constants with at least one of a charge magnitude, dopant concentration, trap density, or charge carrier characteristic of the sample.

22. A system as in claim 21, wherein said first light source is operated so as to simultaneously provide a plurality of pump light pulses to the area of the sample such that constructive and destructive interference results, thereby causing a variation in a density of charge carriers in the sample due to absorption of the plurality of pump light pulses.

23. A system as in claim 21, wherein the same or a different data processor is operated to model at least an effect of an electric field on charge carrier motion within the semiconductor material, and an effect of the charge carriers on at least one optical response of the semiconductor material.

24. A system as in claim 21, wherein said detector and data processor are operated to measure at least one change in an optical response of the semiconductor material, including a change in at least one of $\Delta R(t)$ in an optical reflectivity, a shift $\delta\phi(t)$ in a phase of reflected or transmitted light, a change in a polarization state of reflected light, or a change in direction of reflected or transmitted light, as indicated by probe light pulses individual ones of which are applied at some time t following the absorption of an individual one of the pump light pulses, the probe light pulses being applied at one of the first location or a second location of the semiconductor material.

25. A system as in claim 21, wherein the semiconductor material contains a p-n junction, and wherein the same or a different data processor is operated to model at least an effect of an electric field on charge carrier motion within the semiconductor material, and an effect of the charge carriers on at least one optical response of the semiconductor material, wherein said detector and data processor are operated to measure at least one change in an optical response of the semiconductor material, including a change in at least one of $\Delta R(t)$ in an optical reflectivity, a shift $\delta\phi(t)$ in a phase of reflected or transmitted light, a change in a polarization state of reflected light, or a change in direction of reflected or transmitted light, as indicated by probe light pulses individual ones of which are applied at some time t following the absorption of an individual one of the pump light pulses, the probe light pulses being applied at one of the first location or a second location of the semiconductor material; and wherein said data processor is further operated to compare the measured change in at least one of the reflectivity, phase, polarization state, or direction with changes predicted by the model, and to iterate the model until the changes predicted by the model agree with the measured changes, and to associate measured changes in the optical response with at least one characteristic of the p-n junction.

26. A system as in claim 25, wherein the at least one characteristic of the p-n junction is at least one of a presence of electrically active impurities, a dopant distribution; a dopant concentration; a metallurgical width of the p-n junction; or a permittivity of the semiconductor material.

27. A system as in claim 25, wherein the data processor is further operated to model an effect of an optical response of the semiconductor material to at least one of an electric field due to a dopant distribution within the semiconductor material; an electric field due to electrically charged defects within the semiconductor material; an electric field due to charges in a surface oxide layer that is disposed over a surface of the semiconductor material; a diffusion rate or a charge carrier recombination rate.

28. A system as in claim 21, wherein said data processor associates the measured change with at least one of a minority carrier lifetime or a surface recombination velocity, and subsequently relates the minority carrier lifetime or surface recombination velocity with an impurity concentration or defect concentration within the semiconductor material.

29. A system as in claim 21, wherein the pump light pulses and the probe light pulses have a duration of between about 0.01 to 100 picoseconds.

* * * * *

UNITED STATES PATENT AND TRADEMARK OFFICE
Certiicate

Patent No. 6,008,906                                                  Patented: December 28, 1999

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Humphrey J. Maris and Jackson Loomis.

Signed and Sealed this Twenty-Eighth Day of November, 2000.

DONALD T. HAJEC
*Supervisory Patent Examiner*
Art Unit 2876